United States Patent
Itoh et al.

(10) Patent No.: US 7,071,294 B1
(45) Date of Patent: Jul. 4, 2006

(54) TUMOR ANTIGEN PROTEIN ART-1 AND TUMOR ANTIGEN PEPTIDE THEREOF

(75) Inventors: Kyogo Itoh, Saga-ken (JP); Shinya Gomi, Soja (JP)

(73) Assignee: Green Peptide Co., Ltd., Fukuoka-Ken (JP)

( * ) Notice: Subject to any disclaimer, the term of this patent is extended or adjusted under 35 U.S.C. 154(b) by 0 days.

(21) Appl. No.: 09/857,308

(22) PCT Filed: Nov. 30, 1999

(86) PCT No.: PCT/JP99/06682

§ 371 (c)(1),
(2), (4) Date: Jun. 1, 2001

(87) PCT Pub. No.: WO00/32770

PCT Pub. Date: Aug. 6, 2000

(30) Foreign Application Priority Data

Dec. 1, 1998 (JP) .................................. 10-341253

(51) Int. Cl.
A61K 38/00 (2006.01)
A01N 61/00 (2006.01)
(52) U.S. Cl. ......................................... 530/300; 514/2
(58) Field of Classification Search ............. 424/184.1, 424/185.1; 514/2, 12; 530/300
See application file for complete search history.

(56) References Cited

FOREIGN PATENT DOCUMENTS

| EP | 0911397 A1 | 4/1999 |
|---|---|---|
| EP | 1041146 A1 | 4/2000 |
| EP | 1055684 A1 | 11/2000 |
| WO | 97/46676 | 12/1997 |
| WO | 99/29715 | 6/1999 |
| WO | 99/33977 | 7/1999 |
| WO | WO 99/45954 | * 9/1999 |
| WO | 99/54461 | 10/1999 |

OTHER PUBLICATIONS

Evans et al Q.J.Med 1999;92:299-307.*
Gura (Science, v278, 1997, pp. 1041-1042).*
Nagase et al (DNA Res. Oct. 1998 ; 5(5):277-286).*
Merriam-Webster Online "composition".*
Gene Number (KIAA): 0764, Acc. No. ABO18307.
Nakao et al., "HLA A2601-restricted CTLs Recognize a Peptide Antigen Expressed on Squamous Cell Carcinoma"; Cancer Research; vol. 55, pp. 4248-4252; (1995).
Kubo et al., "Definition of Specific Peptide Motifs for Four Major HLA-A Alleles"; J.of Immunology, vol. 152, pp. 3913-3924 (1994).
Kondo et al., "Prominent Roles of Secondary Anchor Residues in Peptide Binding to HLA-A24 Human Class I Molecules"; J.of Immunology, vol. 155, pp. 4307-4312 (1995).
Sudo et al., "Differences in MHC Class I Self Peptide Repertoires among HLA-A2 Subtypes"; The J. of Immunology, vol. 155, pp. 4749-4756 (1995).
Rivoltini et al., "Induction of Tumor-Reactive CTL from peripheral Blood and Tumor-infiltrating Lymphocytes of Melanoma Patients by In Vitro Stimulation with an Immunodominant Peptide of the Human Melanoma Antigen MART-1", The J. of Immunology, vol. 154, pp. 2257-2265 (1995).
Kharkevitch et al., "Characterization of Autologous Tumor-Specific T-Helper 2 Cells in Tumor-Infiltrating Lymphocytes from a patient with Metastatic Melanoma", Int.J.Cancer, vol. 58, pp. 317-323 (1994).
Thomsen et al., "Delivery of Multiple CD8 Cytotoxic T Cell Epitopes by DNA Vaccination", The J. of Immunology, vol. 160, pp. 1717-1723 (1998).
Tsai et al., "Identification of Subdominant CTL Epitopes of the GP100 Melanoma-Associated Tumor Antigen by Primary in Vitro Immunization with Peptide-Pulsed Dendritic Cells", The J. of Immunology, vol. 158, pp. 1796-1802 (1997).
Rosenberg et al., " Treatment of Patients with Metastatic Melanoma with Autologous Tumor-Infiltrating Lymphocytes and Interleukin 2", J.Natl.Cancer Inst., vol. 86, pp. 1159-1166 (1994).
Altman et al., "Phenotypic Analysis of Antigen-Specific T Lymphocytes", Science, vol. 274, pp. 94-96 (1996).
Rammensee et al., "MHC ligands and peptide motifs: first listing"; Immunogenetics, vol. 41, pp. 178-228 (1995).
Rammensee et al., Immunogenetics, vol. 41, pp. 178-228, (1995).
Nagase, T. et al., DNA Res. (Oct. 30, 1998) vol. 5, p.277-286.
Shichijo, S et al. J. Exp. Med. (Feb. 1998) vol. 187, No. 3, p.277-288.

* cited by examiner

Primary Examiner—Jeffrey Siew
Assistant Examiner—C. Yaen
(74) Attorney, Agent, or Firm—Birch, Stewart, Kolasch & Birch, LLP

(57) ABSTRACT

A novel tumor antigen protein and gene therefor, tumor antigen peptides derived from said tumor antigen protein or derivatives thereof as well as medicaments, prophylactics, or diagnostics for tumors using such tumor substances in vivo or in vitro are provided.

10 Claims, No Drawings

TUMOR ANTIGEN PROTEIN ART-1 AND TUMOR ANTIGEN PEPTIDE THEREOF

This application is the national phase under 35 U.S.C. § 371 of PCT International Application No. PCT/JP99/06682 which has an International filing date of Nov. 30, 1999, which designated the United States of America and was published in English.

TECHNICAL FIELD

The present invention relates to the novel tumor antigen protein, and tumor antigen peptides thereof. More particularly, it relates to the novel tumor antigen protein and the gene thereof, tumor antigen peptides derived from the tumor antigen protein, and derivatives of their substances, as well as to medicaments, prophylactics, or diagnostics for tumors wherein such tumor antigen protein, genes, tumor antigen peptides, or derivatives thereof are utilized in vivo or in vitro.

BACKGROUND ART

It is known that immune system, especially T cells, plays an important role in tumor elimination by a living body. Indeed, infiltration of lymphocytes exhibiting cytotoxic effects on tumor cells in human tumor foci has been observed (*Arch. Surg.*, 126:200, 1990), and cytotoxic T lymphocytes (CTLs) recognizing autologous tumor cells have been isolated from melanomas without great difficulties (e.g., *Immunol. Today*, 8:385, 1987; *J. Immunol.*, 138: 989, 1987; and *Int. J. Cancer*, 52:52, 1992). In addition, the results of clinical trial of melanomas by transfer of such CTLs also suggest the importance of T cells in tumor elimination (*J. Natl. Cancer. Inst.*, 86:1159, 1994).

Although it had long been unknown about target molecules for CTLs attacking autologous tumor cells, the recent advance in immunology and molecular biology gradually began elucidating such target molecules. Specifically, it has been found that CTLs, using the T cell receptors (TCRs), recognize a complex between a peptide, called tumor antigen peptide, and a major histocompatibility complex class I antigen (MHC class I antigen, and in the case of human, referred to as HLA antigen), and thereby attack autologous tumor cells.

Tumor antigen peptides are generated by processing of tumor antigen proteins that are proteins specific for tumors in cells with proteasomes, which proteins are intracellularly synthesized. The tumor antigen peptides thus generated bind to MHC class I antigens (HLA antigens) in endoplasmic reticulum to form complexes, and the complexes are transported to the cell surface to be presented as an antigen. A tumor-specific CTL recognizes the complex presented as an antigen, and exhibits anti-tumor effects through its cytotoxic action or production of lymphokines. As a consequence of elucidation of a series of the actions, it has become possible to treat tumors by using tumor antigen proteins or tumor antigen peptides as so-called cancer vaccines to enhance tumor-specific CTLs in the body of a tumor patient.

As a tumor antigen protein, T. Boon et al. identified a protein named MAGE from human melanoma cells for the first time in 1991 (*Science*, 254:1643, 1991). Subsequently, several additional tumor antigen proteins have been identified mainly from melanoma cells. Examples of melanoma antigens that have been identified are melanosomal proteins such as a melanocytic tissue-specific protein, gp100 (*J. Exp. Med.*, 179:1005, 1994), MART-1 (*Proc. Natl. Acad. Sci. USA*, 91:3515, 1994), and tyrosinase (*J. Exp. Med.*, 178:489, 1993); MEGE-related proteins that are expressed not only on melanomas but also on various cancer cells and normal testicular cells (*J. Exp. Med.*, 179:921, 1994); β-catenin having a tumor-specific amino acid mutation (*J. Exp. Med.*, 183:1185, 1996); and CDK4 (*Science*, 269:1281, 1995). Tumor antigen proteins other than those from melanomas have also been identified, including products of oncogenes such as HER2/neu (*J. Exp. Med.*, 181:2109, 1995) and p53 (variant) (*Proc. Natl. Acad. Sci. USA*, 93:14704, 1996); tumor markers such as CEA (*J. Natl. Cancer Inst.*, 87:982, 1995) and PSA (*J. Natl. Cancer Inst.*, 89:293, 1997); and viral proteins such as HPV (*J. Immunol.*, 154:5934, 1995) and EBV (*Int. Immunol.*, 7:653, 1995). Detailed descriptions of these substances are found in published reviews (e.g. *Immunol. Today*, 18:267, 1997; *J. Exp. Med.*, 183:725, 1996; and *Curr. Opin. Immunol.*, 8:628, 1996).

In applications of a tumor antigen protein or a tumor antigen peptide to treatment or diagnosis of tumors, it is important to identify a tumor antigen that can be widely applied to squamous cell carcinomas such as esophageal and lung cancers that occur at a much higher incidence compared to melanomas. In this relation, the present inventors conducted cloning of a gene encoding a tumor antigen protein from squamous cell carcinoma cells derived from esophageal cancer, and identified for the first time from the tumor cell other than melanomas several tumor antigen peptides that are bound to and presented on HLA antigens of which HLA types are HLA-A24 or HLA-A26 (*J. Exp. Med.*, 187:277, 1998; International Patent Publication WO 97/46676).

When these tumor antigen peptides are clinically applied in practice, it is necessary to utilize a tumor antigen peptide compatible with an individual patient, and it may be desirable to use two or more different tumor antigen peptides rather than to use merely one peptide. That is to say, taking into consideration the facts that all cancer cells do not express an identical tumor antigen in common and that two or more different tumor antigen peptides are presented on a single cancer cell, a treatment using two or more different tumor antigen peptides is believed to be more effective. Indeed, in the case of melanoma, development of cocktail formulations comprising two or more peptides has been attempted, since a single peptide derived from a tumor antigen failed to exhibit adequate effects (*Int. J. Cancer*, 66:162, 1996; and *Int. J. Cancer*, 67:54, 1996). Under such circumstances, it is being required to identify novel tumor antigen proteins and tumor antigen peptides that can be widely applied to epidermal carcinomas such as lung cancers that occur at a higher incidence.

DISCLOSURE OF THE INVENTION

The present invention aims to provide the novel tumor antigen protein and tumor antigen peptides. Particularly, it aims to provide the novel tumor antigen protein and gene thereof, tumor antigen peptides derived from the tumor antigen protein, and derivatives of their substances, as well as to medicaments, prophylactics, or diagnostics for tumors wherein such tumor antigen protein, genes, tumor antigen peptides, or derivatives thereof are utilized in vivo or in vitro. The tumor antigen peptides of the present invention include a tumor antigen peptide that is bound to and presented on HLA-A24 that is the HLA antigen carried by extensive human subjects (e.g. about 60% of the Japanese people), and, therefore, it can be applied to many patients.

Further, the tumor antigen peptides may be applied to treatment or prevention for diverse tumors such as epidermal carcinomas such as lung cancers, bladder cancers and osteosarcoma, and leukemia, and are expected to have utilities as novel anti-tumor medicaments.

In order to obtain a novel tumor antigen protein and tumor antigen peptides, the inventors of the present application made the following attempts.

First of all, the present inventors established CTL lines from lymphocytes derived from a patient with lung cancer that recognize HLA-A24- or HLA-A2-positive bladder cancers, lung cancers, osteosarcoma, or leukemia cell lines, and named them KG-CTL (deposit number: FERM BP-6725).

Subsequently, the inventors prepared a cDNA library from bladder cancer cell line HT-1376 that is strongly reactive to KG-CTL as mentioned above, and doubly transfected COS-7 cell with a recombinant plasmid from the library and a recombinant plasmid containing the cDNA of HLA-A2402 (one type of HLA-A24). The resulting transfectants were treated with KG-CTL as mentioned above, and the amount of produced IFN-γ was measured to determine whether or not KG-CTL was activated. As a result of such screening repeatedly conducted, the present inventors finally succeeded in cloning one gene encoding a tumor antigen protein. The sequencing of the gene revealed that the gene encoding the tumor antigen protein was a novel one. The inventors named the tumor antigen protein encoded by the gene "ART-1" (Adenocarcinoma antigen Recognized by T cells-1).

Further, the present inventors identified tumor antigen peptide portions residing in the amino acid sequence of ART-1 that are bound to and presented on HLA-A24, and demonstrated that such peptides have activity as a tumor antigen peptide.

The present invention has been completed on the basis of the findings as described above.

Thus, the present invention relates to:

(1) A DNA encoding a protein consisting of an amino acid sequence shown in SEQ ID NO: 1, or a protein variant consisting of an amino acid sequence containing substitution, deletion, and/or addition of one or more amino acid residues of SEQ ID NO: 1, provided that the protein and the protein variant give rise to, through its intracellular processing, tumor antigen peptides that are capable of binding to an HLA antigen and being recognized by cytotoxic T lymphocytes;

(2) A DNA consisting of a base sequence shown in SEQ ID NO: 2, a foreign DNA carried in *E. coli* JM 109 (3D9) (deposit number FERM BP-6929), or a DNA variant that hybridizes to the DNAs under a stringent condition, provided that a protein produced and expressed by the DNAs or the DNA variant gives rise to, through its intracellular processing, tumor antigen peptides that are capable of binding to an HLA antigen and being recognized by cytotoxic T lymphocytes;

(3) An expression plasmid that contains the DNA of the above (1) or (2);

(4) A transformant that is transformed with the expression plasmid of the above (3);

(5) A process for producing a recombinant protein, which comprises culturing the transformant of the above (4), and recovering the expressed recombinant protein;

(6) A tumor antigen protein that is encoded by the DNA of the above (1) or (2), or is produced by the process of the above (5);

(7) A pharmaceutical composition that comprises as an active ingredient the DNA of the above (1) or (2), or the protein of the above (6);

(8) A pharmaceutical composition for treating or preventing tumors, which comprises as an active ingredient the DNA of the above (1) or (2), or the protein of the above (6);

(9) A tumor antigen peptide that is a partial peptide derived from the protein of the above (6), and that is capable of binding to an HLA antigen and being recognized by cytotoxic T lymphocytes, or a derivative thereof having the functionally equivalent properties;

(10) The tumor antigen peptide of the above (9) wherein the HLA antigen is HLA-A24, or a derivative thereof having the functionally equivalent properties;

(11) The tumor antigen peptide of the above (10), which comprises a sequence selected from all or part of an amino acid sequence shown in any one of SEQ ID NOs: 3–18, or a derivative thereof having the functionally equivalent properties;

(12) The tumor antigen peptide of the above (11), which comprises a sequence selected from all or part of an amino acid sequence shown in any one of SEQ ID NOs: 3–5, or a derivative thereof having the functionally equivalent properties;

(13) The tumor antigen peptide derivative of the above (11), which comprises a sequence selected from all or part of an amino acid sequence shown in any one of SEQ ID NOs: 3–18 wherein the amino acid residue at position 2 and/or the C-terminus is substituted by another amino acid residue;

(14) The tumor antigen peptide derivative of the above (13), which comprises a sequence selected from all or part of an amino acid sequence shown in any one of SEQ ID NOs: 3–5 wherein the amino acid residue at position 2 and/or the C-terminus is substituted by another amino acid residue;

(15) The tumor antigen peptide derivative of the above (13), which comprises a sequence selected from all or part of an amino acid sequence shown in any one of SEQ ID NOs: 3–18 wherein the amino acid residue at position 2 is substituted by tyrosine, phenylalanine, methionine, or tryptophan, and/or the amino acid residue at the C-terminus is substituted by phenylalanine, leucine, isoleucine, tryptophan, or methionine;

(16) The tumor antigen peptide derivative of claim 14, which comprises a sequence selected from all or part of an amino acid sequence shown in any one of SEQ ID NOs: 19–21;

(17) A pharmaceutical composition for treating or preventing tumors, which comprises as an active ingredient at least one of substances selected from the tumor antigen peptides and derivatives thereof according to any one of the above (9) to (16);

(18) A recombinant DNA comprising at least one of DNAs that encode the tumor antigen peptides or derivatives thereof according to any one of the above (9) to (16);

(19) A recombinant polypeptide obtainable by expressing the recombinant DNA of the above (18);

(20) A pharmaceutical composition for treating or preventing tumors, which comprises as an active ingredient the recombinant DNA of the above (18) or the recombinant polypeptide of the above (19);

(21) An antibody that specifically binds to any one of the protein of the above (6), and the tumor antigen peptide or the derivative thereof according to any one of the above (9) to (16);

(22) An antigen-presenting cell wherein a complex between an HLA antigen and the tumor antigen peptide or the derivative thereof according to any one of the above (9) to (16) is presented on the surface of a cell having antigen-presenting ability, which cell is isolated from a tumor patient;

(23) An antigen-presenting cell on which a complex between an HLA antigen and a tumor antigen peptide or a derivative thereof is presented, said antigen-presenting cell being obtainable by allowing a cell having antigen-presenting ability isolated from a tumor patient to be incorporated with the DNA of the above (1) or (2), the tumor antigen protein of the above (6), the recombinant DNA of the above (18), or the recombinant polypeptide of the above (19);

(24) A pharmaceutical composition for treating tumors, which comprises as an active ingredient the antigen-presenting cell of the above (22) or (23);

(25) A cytotoxic T lymphocyte that specifically recognizes a complex between an HLA antigen and the tumor antigen peptide or derivative thereof according to any one of the above (9) to (16);

(26) A cytotoxic T lymphocyte that specifically recognizes a complex between an HLA antigen and a tumor antigen peptide or derivative thereof, which complex is presented on the antigen-presenting cell of the above (22) or (23);

(27) A pharmaceutical composition for treating tumors, which comprises as an active ingredient the cytotoxic T lymphocyte of the above (25) or (26);

(28) A diagnostic agent for tumors, which comprises the tumor antigen peptide or derivative thereof according to any one of the above (9) to (16), the protein of the above (6), or the recombinant polypeptide of the above (19).

The DNAs of the present invention encode novel tumor antigen proteins, and include a DNA encoding the protein consisting of an amino acid sequence shown in SEQ ID NO: 1, or a protein variant consisting of an amino acid sequence containing substitution, deletion, and/or addition of one or more amino acid residues of the amino acid sequence of SEQ ID NO: 1, provided that the protein and the protein variant give rise to, through its intracellular processing, tumor antigen peptides that are capable of binding to an HLA antigen and being recognized by cytotoxic T lymphocytes; or a DNA consisting of a base sequence shown in SEQ ID NO: 2, a foreign DNA carried in *E. coli* JM 109 (3D9), or a DNA variant that hybridizes to these DNAs under a stringent condition, provided that a protein produced and expressed by the DNA and the DNA variant gives rise to, through its intracellular processing, tumor antigen peptides that are capable of binding to an HLA antigen and being recognized by cytotoxic T lymphocytes. The DNAs of the present invention are further described hereinafter following the order established above.

1) DNA Encoding ART-1

"DNA encoding a protein consisting of an amino acid sequence shown in SEQ ID NO: 1" and "a DNA consisting of a base sequence shown in SEQ ID NO: 2" among the DNAs described above refers to a DNA encoding tumor antigen protein ART-1 from human being of the present invention. The DNA may be cloned in accordance with the process described in Examples hereinafter. Further, the DNA may be also cloned by screening a cDNA library derived from cell lines such as bladder cancer cell line HT-1376 (ATCC No. CRL1472) using an appropriate portion of the base sequence as shown in SEQ ID NO: 2 as a probe for hybridization or a PCR primer. It would be ready for those skilled in the art to achieve such cloning in accordance with Molecular Cloning 2nd Edt. Cold Spring Harbor Laboratory Press (1989), for example.

*E. coli* JM109 (3D9) comprising a plasmid incorporated with ART-1 DNA mentioned above as a foreign DNA has been deposited at The National Institute of Bioscience and Human Technology (1-1-3 Higashi, Tsukuba, Ibaraki, Japan) (deposit number: FERM BP-6929, deposition date: Nov. 25, 1998) (date of conversion to international deposition: Nov. 4, 1999, deposit number: FERM BP-6929).

2) DNA Encoding a Modified Protein of ART-1 or an Allelic Variant Thereof

"DNA encoding a protein variant consisting of an amino acid sequence containing substitution, deletion, and/or addition of one or more amino acid residues of the amino acid sequence shown in SEQ ID NO: 1" among the DNAs described above refers to a DNA that encodes a so-called modified protein, which is artificially prepared, or proteins such as an allelic variant existing in a living body. Number of amino acid residue to be substituted, deleted and/or added should be in a range that enables the substitution, deletion, and/or addition in accordance with the well-known methods such as site-directed mutagenesis hereinafter. It is preferred that one to dozens of an amino acid residue is(are) substituted, deleted and/or added, and it is more preferred that one to several amino acid residue is(are) substituted, deleted and/or added. Substitution is preferably conducted with a conservative amino acid (having a side chain possessing the similar property) that affect no activity.

The DNA encoding such protein variants may be prepared by diverse methods such as site-directed mutagenesis and PCR technique that are described in Molecular Cloning: A Laboratory Manual 2nd Edt. vols. 1–3, Cold Spring Harbor Laboratory Press (1989).

3) DNA that Hybridizes to the DNA of ART-1 Under a Stringent Condition

"DNA variant that hybridizes to a DNA consisting of a base sequence shown in SEQ ID NO: 2, or a foreign DNA carried in *E. coli* JM 109 (3D9) under a stringent condition" among the DNAs described above refers to a DNA that hybridizes to human ART-1 cDNA as shown above under a stringent condition, including ART-1 DNAs from all of vertebrate such as rat and mouse. Further, those variants include a DNA which has an identity of human ART-1 DNA as shown above by 60% or more, 70% or more, 80% or more, or 90% or more, and which hybridizes to human ART-1 DNA under a stringent condition.

In this connection, the term "stringent condition" refers to a condition such that a hybridization is conducted in a solution containing 6×SSC (20×SSC represents 333 mM sodium citrate, 333 mM NaCl), 0.5% SDS and 50% formamide at 42° C., and then the hybridized products are washed in a solution of 0.1×SSC, 0.5% SDS at 68° C., or to conditions as described in Nakayama, et al., *Bio-Jikken-Illustrated*, vol. 2, "Idenshi-Kaiseki-No-Kiso (A Basis for Gene Analysis)", pp. 148–151, Shujunsha, 1995.

The DNA variants are cloned by various methods such as hybridization to the DNA shown in SEQ ID NO: 2. Particular procedures for the methods such as production of cDNA library, hybridization, selection of positive colony, and determination of base sequence are well-known, and may be conducted consulting Molecular Cloning as shown above. Probes useful for the hybridization includes a DNA comprising a base sequence described in SEQ ID NO: 2, or a foreign DNA carried in E. coli JM 109 (3D9).

Among the DNAs as described above 1) to 3), a DNA having an ability to generate a tumor antigen peptide that is capable of binding to an HLA antigen and being recognized by CTLs, and that is derived from a protein produced by the expression of the DNA via intracellular processing, constitutes the DNA encoding tumor antigen protein of the present invention, namely, the DNA of the present invention.

Particularly, the DNAs of the present invention are those that generate such peptide fragment as a partial peptide consisting of a part of an amino acid sequence of a protein produced by the expression of said DNA, said peptide being capable of binding to an HLA antigen, and inducing production of cytotoxic actions and cytokines from CTLs specific for the complex between the peptide and the HLA antigen when binding to the HLA antigen to present on the cell surface.

In this context, determination whether or not a candidate DNA may be a DNA encoding a tumor antigen protein, may be achieved for example by the following method.

First of all, an expression plasmid containing a candidate DNA and an expression plasmid containing a DNA encoding an HLA antigen are doubly transfected into COS-7 (ATCC CRL 1651) derived from African green monkey kidney or fibroblast VA-13 (RIKEN CELL BANK, The Institute of Physical and Chemical Research). The transfection may be achieved by, for example, the Lipofectin method using Lipofectamine reagent (GIBCO BRL). Subsequently, a tumor-responsive CTL that is restricted to the particular HLA antigen used is added to act on the transfectants, and then the amount of various cytokines (for example, IFN-γ) produced by said CTL in response to the transfectants may be measured, for example, by ELISA to determine whether or not the candidate DNA is a DNA of the present invention. Since ART-1 contains HLA-A24-restricted tumor antigen peptide portions, HLA-A24 cDNA (*Cancer Res.*, 55:4248–4252 (1995); Genbank Accession No. M64740) may be used as the above DNA encoding the HLA antigen, whereas those CTLs that are prepared from human peripheral blood lymphocytes as well as HLA-A24-restricted CTLs such as KG-CTL (FERM BP-6725) may be used as the above CTL.

Particular example of the determination for the activity as shown above is further described in Example 2 hereinafter.

The DNA of the present invention as described above can be used as an active ingredient in a medicament or a pharmaceutical composition. In accordance with "pharmaceutical composition" that comprises the DNA of the present invention as an active ingredient, administration of the DNA of the present invention to a tumor patient makes treatment or prevention of tumors possible.

By administering a DNA of the present invention incorporated into an expression vector to a tumor patient according to the following method, the tumor antigen protein is highly expressed in antigen-presenting cells. Tumor antigen peptides that are subsequently generated by intracellular processing bind, to HLA antigen to form complexes, and the complexes are densely presented on the antigen-presenting cell surface. As a result, CTLs specific for the complex efficiently proliferate in the body, and destroy tumor cells. In this way, treatment of tumors, or prevention of tumor proliferation and metastasis is achieved.

Administration and introduction of the DNA of the present invention into cells may be achieved using viral vectors or according to any one of other procedures (*Nikkei-Science*, April, 1994, pp. 20–45; *Gekkan-Yakuji*, 36(1), 23–48 (1994); *Jikken-Igaku-Zokan*, 12(15), 1994, and references cited therein).

Examples of the methods using viral vectors include methods in which the DNA of the present invention is incorporated into DNA or RNA viruses such as retrovirus, adenovirus, adeno-associated virus, herpesvirus, vaccinia virus, poxvirus, poliovirus, or Sindbis virus, and introduced into cells. Among these methods, those using retrovirus, adenovirus, adeno-associated virus, or vaccinia virus are especially preferred.

Other methods include those in which expression plasmids are directly injected intramuscularly, liposome method, Lipofectin method, microinjection, calcium phosphate method, and electroporation, and DNA vaccination and liposome method is especially preferred.

In order to allow a DNA of the present invention to act as a medicament in practice, an in vivo method in which DNA is directly introduced into the body, and an ex vivo method in which DNA is extracorporeally introduced into certain cells that have been removed from human, and the cells are reintroduced into the body, are used (*Nikkei-Science*, April, 1994, pp. 20–45; *Gekkan-Yakuji*, 36(1), 23–48 (1994); *Jikkenn-Igaku-Zokan*, 12(15), 1994; and references cited therein). An in vivo method is more preferred.

In case of in vivo methods, the DNA may be administered by any appropriate route depending on the disease and symptoms to be treated and other factors. For example, it may be administered via intravenous, intraarterial, subcutaneous, intracutaneous, intramuscular route, or the like. In the case of in vivo methods, the compositions may be administered in various dosage forms such as solution, and are typically formulated, for example, in the form of injection containing DNA of the present invention as an active ingredient, said formulation may contain conventional carriers, if necessary. If a DNA of the present invention is included in liposomes or membrane-fused liposomes (such as Sendai virus (HVJ)-liposomes), the compositions may be in the form of liposome formulations such as suspension, frozen drug, centrifugally-concentrated frozen drug, or the like.

Although the amount of a DNA of the present invention in such formulations may vary depending on the disease to be treated, the age and the weight of the patient, and the like, it is typical to administer 0.0001 mg–100 mg, preferably 0.001 mg–10 mg, of a DNA of the present invention every several days to every several months.

In the invention, the term "protein" refers to a protein encoded by the diverse DNAs of the present invention as described above, which has an ability as tumor antigen protein to give rise to tumor antigen peptides via intracellular processing that are capable of binding to an HLA antigen and being recognized by CTLs. Specific examples of the proteins include ART-1 consisting of an amino acid sequence shown in SEQ ID NO: 1. The proteins of the present invention may be produced in large scale using the DNA of the present invention as described above.

Production of tumor antigen proteins by expressing the DNA of the present invention may be achieved in accordance with many publications and references such as "Molecular Cloning" mentioned above. Particularly, an expression plasmid is constructed by inserting a DNA of the present invention into an appropriate expression vector (e.g., pSV-SPORT1, pCR3). Subsequently, the expression plasmid is introduced into appropriate host cells to obtain transformants. Examples of host cells include those cells of prokaryotes such as *Escherichia coli*, unicellular eukaryotes such as yeast, and multicellular eukaryotes such as insects or animals. Transfer of expression plasmid into host cells may be achieved by conventional methods such as calcium phosphate method, DEAE-dextran method, electric pulse method, Lipofectin method, or the like. Desired proteins are produced by culturing the transformants in appropriate medium according to usual methods. The tumor antigen proteins thus obtained may be isolated and purified according to standard biochemical procedures.

It can be demonstrated whether or not a tumor antigen protein of the present invention as prepared above has certain activity by, as described above, expressing the DNA of the present invention within cells to produce the protein of the present invention, and determining if a peptide fragment generated by intracellular processing of said protein has the activity as a tumor antigen peptide. In case of using the tumor antigen protein as it is, the measurement for the activity can be achieved by allowing the protein to be incorporated into the phagocytes such as macrophage so as to generate peptide fragments in cells, and then contacting CTLs to complexes between the peptide fragments and the HLA antigen, followed by measuring the amount of various cytokines (for example, IFN-γ) produced by the CTLs in response to the complexes.

The protein of the present invention as described above can be also used as an active ingredient in medicament or a pharmaceutical composition. In accordance with "pharmaceutical composition" that comprises the protein of the present invention as an active ingredient, administration of the protein of the present invention makes treatment or prevention of tumors possible, for example. When administered to a tumor patient, the protein of the present invention is introduced into antigen-presenting cells. Tumor antigen peptides that are subsequently generated by intracellular processing bind to HLA antigen to form complexes, and the complexes are presented on the cell surface. CTLs specific for the complex efficiently proliferate in the body, and destroy tumor cells. In this way, treatment of tumors or prevention of tumor proliferation and metastasis is achieved.

Pharmaceutical compositions comprising the tumor antigen protein of the present invention may be administered together with an adjuvant in order to effectively establish the cellular immunity, or may be administered in a particulate dosage form. For such purpose, those adjuvants described in the literature (*Clin. Microbiol. Rev.*, 7:277–289, 1994) are applicable. In addition, liposomal preparations, particulate preparations in which the ingredient is bound to beads having a diameter of several µm, or preparations in which the ingredient is attached to lipids are also possible. Administration may be achieved, for example, intradermally, hypodermically, or by intravenous injection. Although the amount of a tumor antigen protein of the present invention in such formulations may vary as appropriate depending on the disease to be treated, the age and the weight of the patient, and the like, it is typical to administer 0.0001 mg–1000 mg, preferably 0.001 mg–100 mg, more preferably 0.01 mg–10 mg of a tumor antigen protein of the present invention every several days to every several months.

In the present invention, the term "tumor antigen peptide" refers to a partial peptide which consists of a part of the tumor antigen protein of the present invention and which is capable of binding to an HLA antigen and being recognized by CTL. Accordingly, any peptide falls within the scope of the tumor antigen peptide of the present invention, regardless of its length or its position in the amino acid sequence of the present protein, as long as the peptide consists of a part of the amino acid sequence of the present protein, and a complex between said peptide and an HLA antigen is capable of being recognized by CTL. Such tumor antigen peptides of the present invention can be identified by synthesizing a candidate peptide which consists of a part of the tumor antigen protein of the present invention, and conducting an assay for determining whether or not a complex between the candidate peptide and an HLA antigen is recognized by CTL, in other words, whether or not the candidate peptide has the activity as a tumor antigen peptide.

In this connection, synthesis of peptides may be conducted according to a method usually used in peptide chemistry. Examples of such known methods are those described in the literatures including "Peptide Synthesis", Interscience, New York, 1966; "The Proteins", vol. 2, Academic Press Inc., New York, 1976; "Pepuchido-Gosei", Maruzen Co. Ltd., 1975; "Pepuchido-Gosei-no-Kiso-to-Jikkenn", Maruzen Co. Ltd., 1985; and "Iyakuhin-no-Kaihatu, Zoku, vol. 14, Peputido-Gosei", Hirokawa Shoten, 1991.

Next, methods for identifying tumor antigen peptides of the present invention are further described below.

The respective sequence rules (motifs) of antigen peptides that are bound to and presented on the following HLA types have been known; HLA-A 1, -A0201, -A0204, -A0205, -A0206, -A0207, -A11, -A24, -A31, -A6801, -B7, -B8, -B2705, -B37, -Cw0401, and -Cw0602 (see, e.g., *Immunogenetics*, 41:178, 1995). Regarding the motif for HLA-A24, for example, it is known that in the sequence of peptides consisting of 8 to 11 amino acids, the amino acid at position 2 is tyrosine, phenylalanine, methionine, or tryptophan, and the amino acid at the C-terminus is phenylalanine, leucine, isoleucine, tryptophan, or methionine (*J. Immunol.*, 152: 3913, 1994; *Immunogenetics*, 41:178, 1995; *J. Immunol.*, 155:4307, 1994). Likewise, the motifs shown in the following Table 1 are known for HLA-A2 (*Immunogenetics*, 41:178, 1995; *J. Immunol.*, 155:4749, 1995).

TABLE 1

| Type of HLA-A2 | Amino acid at the second position from N-terminus | Amino acid at C-terminus |
| --- | --- | --- |
| HLA-A0201 | L, M | V, L |
| HLA-A0204 | L | L |
| HLA-A0205 | V, L, I, M | L |
| HLA-A0206 | V, Q | V, L |
| HLA-A0207 | L | L |

(the peptides are 8–11 amino acids in length)

Recently, any peptide sequence expected to be capable of binding to HLA antigens can be, further, searched on internet using a software of NIH BIMAS (http://bimas.dcrt.nih.gov/molbio/hla_bind /).

By analysis of antigen peptides bound to various HLA molecules, it has been shown that the length of the peptides is usually about 8 to about 14 amino acids long, although antigen peptides of 14 or more amino acids in length are also observed for HLA-DR, -DP, and -DQ (*Immunogenetics*, 41:178, 1995).

It is easy to select peptide portions involved in such motifs from the amino acid sequence of the protein of the present invention. Such peptide portions involved in the above motif structures can be easily selected by inspecting the amino acid sequence of tumor antigen protein ART-1 (SEQ ID NO: 1). Further, any sequence expected to be capable of binding to HLA antigens can be easily selected by search on internet as shown above. Tumor antigen peptides of the present invention can be identified by synthesizing candidate peptides thus selected according to the method described above, and conducting an assay for determining whether or not a complex between the candidate peptide and an HLA antigen is recognized by CTL, in other words, whether or not a candidate peptide has an activity as a tumor antigen peptide.

A specific example of method for identifying tumor antigen peptides of the present invention is a method described in *J. Immunol.*, 154:2257,1995. Specifically, peripheral blood lymphocytes are isolated from a human who is positive for the type of an HLA antigen that is expected to present the candidate peptide, and are stimulated in vitro by adding the candidate peptide. If the candidate induces CTL that specifically recognizes the HLA-antigen-presenting cells pulsed with the candidate peptide, it is indicated that the particular candidate peptide may function as a tumor antigen peptide. In this connection, the presence or absence of CTL induction can be detected, for example, by measuring the amount of various cytokines (for example, IFN-γ) produced by CTLs in response to the antigen peptide-presenting cells using, for example, an ELISA method. Alternatively, a method in which the cytotoxicity of CTLs against antigen peptide-presenting cells labeled with $^{51}$Cr is measured ($^{51}$Cr release assay, *Int. J. Cancer*, 58:317, 1994) may also be used for such detection.

Furthermore, the detection can also be achieved as follows. An expression plasmid expressing a cDNA for the type of an HLA antigen that is expected to present the candidate peptide is incorporated into, for example, COS-7 cells (ATCC No. CRL1651) or VA-13 cells (RIKEN CELL BANK, The Institute of Physical and Chemical Research), and the resultant cells are pulsed with the candidate peptide. The cells are then reacted with the CTLs that are restricted to the type of the HLA antigen expected to present the candidate peptide as described above, and the amount of various cytokines (for example, IFN-γ) produced by said CTLs is measured (*J. Exp. Med.*, 187:277, 1998).

Specific examples of the detection are further described in Examples 8 and 9 hereinafter.

ART-1 contains HLA-A24-restricted tumor antigen peptide portions. In case of HLA-A24-restricted tumor antigen peptides, the detection of tumor antigen peptides may be achieved by using HLA-A24 cDNA (*Cancer Res.*, 55:4248–4252, 1995, Genbank Accession No. M64740) as a cDNA encoding the HLA antigen described above, and using those CTLs such as KG-CTL (FERM BP-6725) and CTLs that are prepared by peptide-stimulation of human peripheral blood lymphocytes as the CTLs described above.

In cases like HLA-A26 wherein a relevant peptide motif is not elucidated, the method for the identification is different from that in the above cases wherein the sequence rules (motifs) have been elucidated. In such case, tumor antigen peptides of the present invention may be identified, for example, according to the method described in WO 97/46676, provided that a CTL line recognizing a complex between HLA-A26 and a tumor antigen peptide is available.

The methods for identifying tumor antigen peptides as described above may be hereinafter collectively referred to as "assay methods for tumor antigen peptides".

As described above, it is known that the sequences of tumor antigen peptides that are bound to and presented on HLA-A24 obey a certain rule (motif), and, in particular, the motif is that, in a sequence of a peptide consisting of 8 to 11 amino acids, the amino acid at position 2 is tyrosine, phenylalanine, methionine, or tryptophan, and the amino acid at the C-terminus is phenylalanine, leucine, isoleucine, tryptophan, or methionine (*J. Immunol.*, 152:3913, 1994; *Immunogenetics*, 41:p178, 1995; *J. Immunol.*, 155:p4307, 1994). As shown above, sequences expected to be capable of binding to HLA antigens may be further searched on internet using NIH BIMAS software (http://bimas.dcrt.nih.gov/molbio/hla_bind/).

Accordingly, HLA-A24-restricted tumor antigen peptides of the present invention are exemplified by those tumor antigen peptides which are partial peptides involved in such motif structures or structures expected to be capable of binding to the HLA in the amino acid sequence of ART-1 shown in SEQ ID NO: 1 and which are capable of binding to HLA-A24 antigens and being recognized by CTLs.

Particular examples of HLA-A24-restricted tumor antigen peptides described above include those tumor antigen peptides which comprise all or part of an amino acid sequence shown in any one of SEQ ID NOs: 3–18 and which are capable of binding to an HLA-A24 antigen and being recognized by CTL. Specifically, examples are:

1) peptides that consist of an amino acid sequence shown in any one of SEQ ID NOs: 3–18, and
2) peptides that comprise the full length or a consecutive portion of an amino acid sequence shown in any one of SEQ ID NOs: 3–18 and that are elongated in the N-terminal and/or C-terminal direction as compared to said amino acid sequence, or peptides consisting of a consecutive portion of an amino acid sequence shown in any one of SEQ ID NOs: 3–18, said peptides being capable of binding to the HLA-A24 antigen and being recognized by CTLs. The peptides in the above 2) may be about 8–11 amino acids in length in view of the fact that they are bound and presented by the HLA-A24 antigen. "A consecutive portion" includes a part to be bound to the HLA antigen and therefore is preferably a structure not affecting the motif.

Suitable examples of HLA-A24-restricted tumor antigen peptides of the present invention include those tumor antigen peptides that comprise all or part of the amino acid sequence shown in any one of SEQ ID NOs: 3–5 and that are capable of binding to an HLA-A24 antigen and being recognized by CTL. Specifically, examples are:

1) peptides that consist of the amino acid sequence shown in any one of SEQ ID NOs: 3–5, and
2) peptides that comprise the full length or a consecutive portion of the amino acid sequence shown in any one of SEQ ID NOs: 3–5 and that are elongated in the N-terminal and/or C-terminal direction as compared to said amino acid sequence, or peptides that consist of a consecutive portion of the amino acid sequence shown in any one of SEQ ID NOs: 3–5, said peptides being capable of binding to the HLA-A24 antigen and being recognized by CTLs.

In the present invention, the term "derivative having properties functionally equivalent to those of a tumor antigen peptide" (hereinafter may be simply referred to as tumor antigen peptide derivative) refers to an altered peptide, of which the amino acid sequence contains alteration of one or more, preferably one to several, amino acid residues of an amino acid sequence of a tumor antigen peptide of the present invention, and which has the properties as a tumor antigen peptide, that is, capable of binding to an HLA antigen and being recognized by CTL. Accordingly, all tumor antigen peptide derivatives fall within the scope of tumor antigen peptides of the present invention so long as they contains alteration of one or more amino acid residues of an amino acid sequence of a tumor antigen peptide of the present invention, and have the properties as tumor antigen peptides, that is, are capable of binding to HLA antigens and being recognized by CTLs.

In this context, "alteration" of an amino acid residue means substitution, deletion and/or addition (including addition of amino acids to the N-terminus and/or the C-terminus of the peptide) of an amino acid residue, with substitution of an amino acid residue being preferred. For alterations involving substitution of an amino acid residue, although the number and the position of amino acid residues to be substituted may be determined arbitrarily so long as the activity as a tumor antigen peptide is retained, it is preferred that one to several residues are substituted in light of the fact that tumor antigen peptides are usually about 8 to about 14 amino acids in length as described above.

A preferred length of tumor antigen peptide derivatives of the present invention is about 8 to about 14 amino acids similarly to the tumor antigen peptides described above, although derivatives of 14 or more amino acids long may also be possible for HLA-DR, -DP, and -DQ.

Such tumor antigen peptide derivatives of the present invention may be identified by synthesizing altered peptides that contain alteration of a part of a tumor antigen peptide of the present invention in accordance with the above preparation of peptide, and by conducting the above assay for tumor antigen peptides.

As described above, the sequence rules (motifs) for peptides that are bound to and presented on HLA types such as HLA-A1, -A0201, -A0204, -A0205, -A0206, -A0207, -A 1, -A24, -A31, -A6801, -B7, -B8, -B2705, -B37, -Cw0401, and -Cw0602 have been elucidated. As shown above, peptide sequences expected to be capable of binding to HLA antigens may be further searched on internet (http://bimas.dcrt.nih. gov/molbio/hla_bind/). Consequently, tumor antigen peptide derivatives containing the alteration of the amino acids in a tumor antigen peptide of the present invention can be prepared on the basis of such motifs.

For example, regarding the motif for antigen peptides that are bound to and presented on HLA-A24, it is known as described above that in the sequence of a peptide consisting of 8 to 11 amino acids, the amino acid at position 2 is tyrosine, phenylalanine, methionine, or tryptophan, and the amino acid at the C-terminus is phenylalanine, leucine, isoleucine, tryptophan, or methionine (*J. Immunol.*, 152: 3913, 1994; *Immunogenetics*, 41:178, 1995; *J. Immunol.*, 155:4307, 1994). Likewise, the motifs shown in the above Table 1 are known for HLA-A2. In addition, peptide sequences expected to be capable of binding to HLA antigens is laid open on internet (http://bimas.dcrt.nih.gov/molbio/ hla_bind/), and amino acid residues having properties similar to those of amino acids according to the motifs may also be possible. Accordingly, examples of tumor antigen peptide derivatives of the present invention include those peptide derivatives that comprise all or part of an amino acid sequence of the tumor antigen peptide of the present invention in which one or more amino acid residues at any positions that may be allowed for substitution according to the motifs (for HLA-A24 and HLA-A2, position 2 and the C-terminus) are substituted by other amino acids (preferably, those amino acids which are expected to be capable of binding to the antigens according to the above internet), and which derivatives have activity of binding to HLA antigens and being recognized by CTLs. Preferred examples are those tumor antigen peptide derivatives that comprise all or part of an amino acid sequence in which amino acid residues selected from those according to the above motifs are substituted at the above positions, and which derivatives have the above activity. A preferred length of "all or part" of an amino acid sequence is about 8 to about 14 amino acids comprising altered residues, although it may be a length of 14 or more amino acids for HLA-DR, -DP, and -DQ. "Part" includes a portion to be bound to the HLA antigens.

Examples of HLA-A24-restricted tumor antigen peptide derivatives include those peptide derivatives that comprise all or part of an amino acid sequence of a peptide derived from the amino acid sequence of ART-1 having a binding motif for HLA-A24 in which one or more amino acid residues at positions that are allowed for substitution according to the above motifs, specifically, at position 2 and/or the C-terminus, are substituted by other amino acid residues (preferably, which is the amino acid expected to be capable of binding to the antigens according to the above internet), and which derivatives have the above activity. Preferred examples are those tumor antigen peptide derivatives that comprise all or part of an amino acid sequence in which the amino acid residues at position 2 and/or the C-terminus are substituted by the amino acid residues involved according to the above motifs, and which derivatives have the above activity. A preferred length of "all or part" of such HLA-A24-restricteid tumor antigen peptide derivatives is about 8 to about 11 amino acids comprising the altered residues.

In particular, examples are those tumor antigen peptide derivatives that comprise all or part of an amino acid sequence shown in any one of SEQ ID NOs: 3 to 18 in which the amino acid residues at position 2 and/or the C-terminus are substituted by other amino acid residues (preferably, which is the amino acid expected to be capable of binding to the antigens according to internet as shown above), and which derivatives have the above activity. Preferred examples are those tumor antigen peptide derivatives that comprise all or part of an amino acid sequence shown in any one of SEQ ID NOs: 3 to 18 in which the amino acid residues at position 2 and/or the C-terminus are substituted by the amino acid residues involved according to the above motifs, and which derivatives have the above activity. Specifically, examples of HLA-A24-restricted tumor antigen derivatives are those tumor antigen peptide derivatives that comprise all or part of an amino acid sequence shown in any one of SEQ ID NOs: 3 to 18 in which the amino acid residue at position 2 is substituted by tyrosine, phenylalanine, methionine or tryptophan, and/or the amino acid residue at the C-terminus is substituted by phenylalanine, leucine, isoleucine, tryptophan or methionine, and which derivatives have the above activity. More specific examples include those tumor antigen peptide derivatives that consist of an amino acid sequence shown in any one of SEQ ID NOs: 3 to 18 in which the amino acid residue at position 2 is substituted by tyrosine, phenylalanine, methionine or tryptophan, and/or the amino acid residue at the C-terminus is substituted by phenylalanine, leucine, isoleucine, tryptophan or methionine, and which derivatives have the above activity.

Suitable examples of HLA-A24-restricted tumor antigen peptide derivatives of the present invention are those tumor antigen peptide derivatives that comprise all or part of an amino acid sequence shown in any one of SEQ ID NOs: 3 to 5 in which the amino acid residues at position 2 and/or the C-terminus are substituted by other amino acid residues (preferably, which is the amino acid expected to be capable of binding to the antigens according to internet as shown above), and which derivatives have the above activity. More preferred examples are those tumor antigen peptide derivatives comprise all or part of an amino acid sequence shown in any one of SEQ ID NOs: 3 to 5 in which the amino acid residue at position 2 is substituted by tyrosine, phenylalanine, methionine or tryptophan, and/or the amino acid residue at the C-terminus is substituted by phenylalanine, leucine, isoleucine, tryptophan or methionine, and which derivatives have the above activity. Suitable examples of such tumor antigen peptide derivatives are shown in SEQ ID NOs: 19 to 21.

A tumor antigen peptide or its derivative of the present invention can be used solely or together with other one or more of them as a pharmaceutical composition for treating or preventing tumors.

For the purpose of the treatment or prevention for tumors, specifically, at least one or a combination of two or more of a tumor antigen peptide or its derivative of the present invention, together with other tumor antigen peptides, if necessary, is administered to patients. When the pharmaceutical composition for treating or preventing tumors which comprises as an active ingredient a tumor antigen peptide or its derivative of the present invention is administered to a ART-1-positive patient, the tumor antigen peptide or the derivative thereof is presented with an HLA antigen on antigen-presenting cells, and CTLs specific for the presented HLA antigen complex proliferate and destroy the tumor cells. As a result, the pharmaceutical composition enables to treat tumors of patients, or to prevent proliferation or metastasis of tumors. ART-1 is expressed extensively on the epidermal carcinomas such as lung cancer, and therefore, the pharmaceutical composition for treating or preventing tumors according to the present invention is advantageous in terms of wide applicability. The pharmaceutical composition for treating or preventing tumors which comprises as an active ingredient a tumor antigen peptide or its derivative of the present invention also can achieve an increased therapeutic effect by combining with the use of conventional chemotherapy or radiotherapy.

The composition for treating or preventing tumors which comprises as an active ingredient a tumor antigen peptide or its derivative of the present invention may be administered together with an adjuvant in order to effectively establish the cellular immunity, or may be administered in a particulate dosage form. For such purpose, those adjuvants described in the literature (*Clin. Microbiol. Rev., 7*:277–289, 1994) are applicable. In addition, liposomal preparations, particulate preparations in which the ingredient is bound to beads having a diameter of several µm, or preparations in which the ingredient is attached to lipids are also possible. Administration may be achieved, for example, intradermally, hypodermically, or by intravenous injection. Although the amount of a tumor antigen peptide or its derivative of the present invention in the formulation to be administered may be adjusted as appropriate depending on, for example, the disease to be treated, the age and the body weight of the particular patient, it is typical to administer 0.0001 mg to 1000 mg, preferably 0.001 mg to 100 mg, and more preferably 0.01 mg to 10 mg every several days to every several months.

Further, a recombinant DNA that contains at least one DNA encoding a tumor antigen peptide or its derivative of the present invention, or a recombinant polypeptide obtainable by expression of said recombinant DNA may be also comprised as an active ingredient in the pharmaceutical composition for treating or preventing tumors according to the present invention, which details are provided below.

In this connection, the term "recombinant DNA" refers to any DNA encoding a partial polypeptide, a partial peptide consisting of a part of the tumor antigen protein of the present invention, derivatives thereof, polytope in which such peptides are combined, or the like. All DNAs fall within the scope of recombinant DNAs of the present invention so long as they contain at least one DNA encoding the tumor antigen peptide or its derivative of the present invention. Such recombinant DNA may be incorporated into a suitable expression vector to make an active ingredient comprised in the pharmaceutical composition for treating or preventing tumors.

The term "polytope" refers to a combined peptide of many CTL epitopes, and DNAs encoding such polytopes have recently been used for DNA vaccination. See, for example, *J. of Immunology,* 160, p1717, 1998. A DNA encoding the polytope of the present invention can be prepared by ligating one or more DNAs encoding the tumor antigen peptide or its derivative of the present invention each other, and, if desired, ligating it with a DNA encoding other tumor antigen peptide(s).

Recombinant DNAs of the present invention can be easily prepared according to typical DNA synthesis or genetic engineering method, for example, according to the description of a standard text such as "Molecular Cloning", 2nd ed., Cold Spring Harbor Laboratory Press (1989). Incorporation of such recombinant DNAs into expression vectors may be also conducted according to the above standard text and the like.

Determination whether or not a recombinant DNA of the present invention as prepared above may generate tumor antigen peptides that are capable of binding to HLA antigens and being recognized by CTLs may be achieved in accordance with, for example, the method as mentioned above for determining the activity of DNA of the present invention. Likewise, a method for using the present recombinant DNA as medicaments or prophylactics may be in accordance with the method for the DNA of the present invention.

As shown above, "recombinant polypeptide" obtainable by expression of the recombinant DNA of the present invention may also be used for a pharmaceutical composition for treating or preventing tumors.

The recombinant polypeptide of the invention may be prepared in a similar manner to that for the protein of the invention as described above. Likewise, determination whether or not a recombinant polypeptide of the present invention as prepared above may have certain activity may be achieved in accordance with a similar manner to that for the protein of the present invention. Further, a method for using the present recombinant polypeptide as medicaments or prophylactics may be in accordance with the above method for the protein or peptide of the present invention.

A tumor antigen peptide, derivative thereof, tumor antigen protein, a DNA therefor of the present invention, or a recombinant DNA or recombinant polypeptide of the present invention may be used in vitro for treatment of tumor patients as follows.

On usage of a tumor antigen peptide, derivative thereof, tumor antigen protein, or a DNA therefor in treatment of tumors, it is important to establish an administration method which can efficiently induce specific CTLs in the body of a patient. As one of the means therefor, the present invention provides an antigen-presenting cell in which a complex between an HLA antigen and a tumor antigen peptide or its derivative of the present invention is presented on the surface of a cell having antigen-presenting ability isolated from a tumor patient, and also provides a pharmaceutical composition for treating tumors, which comprises said antigen-presenting cell as an active ingredient.

In this context, "cell having antigen-presenting ability" is not limited to a specific cell so long as it is a cell expressing on its cell surface an HLA antigen allowing a tumor antigen peptide or its derivative of the present invention to be presented, and dendritic cells, which is reported to have especially a high antigen-presenting ability, are preferred.

Substances to be added to prepare an antigen-presenting cell of the present invention from the above-mentioned cell having an antigen-presenting ability may be tumor antigen peptides or their derivatives of the present invention, as well as DNAs, proteins, recombinant DNAs or recombinant polypeptides of the present invention. When used in the form of a protein or DNA, it is necessarily incorporated into cells.

In order to prepare antigen-presenting cells of the present invention, cells having an antigen-presenting ability are isolated from a tumor patient, and pulsed ex vivo with a tumor antigen peptide, a derivative thereof, a tumor antigen protein, or recombinant polypeptide of the present invention to present a complex between an HLA antigen and said tumor antigen peptide or derivative thereof (*Cancer Immunol. Immunother.*, 46:82, 1998; *J. Immunol.* 158:p1796, 1997; *Cancer Res.*, 59:1184,1999). When dendritic cells are used, antigen-presenting cells of the present invention may be prepared, for example, by isolating lymphocytes from peripheral blood of a tumor patient using Ficoll method, then removing non-adherent cells, incubating the adherent cells in the presence of GM-CSF and IL-4 to induce dendritic cells, and incubating and pulsing said dendritic cells with a tumor antigen peptide or tumor antigen protein of the present invention.

When antigen-presenting cells of the present invention are prepared by introducing a DNA or a recombinant DNA of the present invention into the aforementioned cells having an antigen-presenting ability, said gene may be in the form of DNA or RNA. In particular, DNA may be used consulting, for example, *Cancer Res.*, 56:5672, 1996 or *J. Immunol.*, 161:p5607, 1998, and RNA may be used consulting, for example, *J. Exp. Med.*, 184:p465, 1996.

A pharmaceutical composition for treating tumors which comprises the above antigen-presenting cells as an active ingredient preferably contains physiological saline, phosphate buffered saline (PBS), medium, or the like to stably maintain the antigen-presenting cells. It may be administered, for example, intravenously, subcutaneously, or intradermally. By reintroducing such composition for treating tumors which comprises antigen-presenting cells as an active ingredient into the body of the patient, specific CTLs are efficiently induced in the ART-1-positive patient so as to achieve treatment of the tumor. It should be undisputed that the HLA types need be compatible between the patient and the peptide used, such that an HLA-A24-restricted tumor antigen peptide or a derivative thereof must be used for an HLA-A24-positive tumor patient.

In addition, in vitro use of a tumor antigen peptide, a derivative thereof, a tumor antigen protein, a DNA therefor, a recombinant DNA or recombinant polypeptide according to the present invention in the following adoptive immunotherapy may be provided as another example of their use.

It has been observed that an adoptive immunotherapy achieves a therapeutic effect of melanomas, wherein tumor-infiltrating T cells taken from the patient himself/herself are cultured ex vivo in large quantities, and then returned into the patient (*J. Natl. Cancer. Inst.*, 86:1159, 1994). Likewise, suppression of metastasis has been observed in mouse melanoma by in vitro stimulation of splenocytes with tumor antigen peptide TRP-2, thereby proliferating CTLs specific for the tumor antigen peptide, and administering said CTLs into a melanoma-grafted mouse (*J. Exp. Med.*, 185:453, 1997). This resulted from in vitro proliferation of CTLs that specifically recognize the complex between an HLA antigen of antigen-presenting cells and the tumor antigen peptide. Accordingly, a method for treating tumors is believed to be useful, which comprises stimulating in vitro peripheral blood lymphocytes from a patient using a tumor antigen peptide, a derivative thereof, a tumor antigen protein, or a DNA therefor according to the present invention to proliferate tumor-specific CTLs, and subsequently returning the CTLs into the patient.

Thus, the present invention provides CTLs that specifically recognize a complex between the HLA antigen and the tumor antigen peptide or derivative thereof, and also provides a pharmaceutical composition for treating tumors which comprises said CTLs as an active ingredient. Such composition preferably contains physiological saline, phosphate buffered saline (PBS), medium, or the like to stably maintain CTLs. It may be administered, for example, intravenously, subcutaneously, or intradermally. By reintroducing the composition for treating tumors which comprises CTLs as an active ingredient into the body of the patient, the toxic effect of CTLs against the tumor cells is enhanced in ART-1-positive patients and thereby destroys the tumor cells to achieve treatment of the tumor.

The present invention also provides antibodies that specifically bind to a protein of the present invention, a tumor antigen peptide of the present invention or a derivative thereof. Such antibodies are easily prepared, for example, according to a method described in "Antibodies: A Laboratory Manual", Lane, H. D. et al. eds., Cold Spring Harbor Laboratory Press, New York, 1989. Specifically, antibodies that recognize a tumor antigen peptide or its derivative of the present invention and additionally antibodies that neutralize their activities may easily be prepared by immunizing appropriately an animal with the tumor antigen peptide or derivative thereof in the usual manner. Such antibodies may be used in affinity chromatography, immunological diagnosis, and the like.

In order to conduct immunological diagnosis as shown above, the antibodies as prepared above are first labeled as appropriate if necessary, and the presence of antigens in a sample taken from a patient suspected to have a tumor (such as blood or a tumor tissue), thus achieving a diagnosis of the presence or absence of a tumor. Specific diagnosis may be conducted via immunoblotting, radioimmunoassay (RIA), enzyme-linked immunosorbent assay (ELISA), a fluorescent or luminescent assay, and the like.

Tumor antigen peptides, derivatives thereof, tumor antigen proteins, or recombinant polypeptide thereof according to the present invention may be also used as an active ingredient of a diagnostic agent for diagnosing tumors. Specifically, by using a tumor antigen peptide, or derivative thereof according to the present invention itself as a diagnostic agent to detect the presence of antibodies in a sample obtained from a patient suspected to have a tumor (such as blood or a tumor tissue), early detection of tumors and diagnosis of recurrence and metastasis of tumors are possible. The same procedure can also be used for selection of tumor patients that can be treated with a medicine comprising as an active ingredient, for example, a tumor antigen peptide of the present invention. In particular, such diagnosis may be conducted using immunoblotting, RIA, ELISA, a fluorescent or luminescent assay or the like.

Furthermore, in recent years, a new detection method has been established for detecting antigen-specific CTLs using a complex between the antigen peptide and an HLA antigen (Science, 274:94,1996). Early detection of tumors and diagnosis of reoccurrence or metastasis are possible by using a complex between a tumor antigen peptide or derivative thereof according to the present invention and an HLA antigen in the above detection method, and thereby detecting tumor antigen-specific CTLs. The same procedure can also be used for selection of tumor patients that can be treated with a medicine comprising as an active ingredient, for example, a tumor antigen peptide of the present invention, or for determination of the therapeutic effect of said medicine. Thus, the present invention also provides a diagnostic agent for tumors comprising a tumor antigen peptide or derivative thereof according to the present invention.

In particular, such diagnosis may be conducted by preparing a tetramer of a complex between an HLA antigen fluorescently labeled according to the method described in the literature (Science, 274:94, 1996) and a tumor antigen peptide, and using it to quantitatively determine the antigen peptide-specific CTLs in peripheral blood lymphocytes of a patient suspected to have a tumor using a flow cytometer.

A DNA encoding a tumor antigen peptide, a tumor antigen protein, a tumor antigen peptide or a derivative thereof, an antigen-presenting cell that presents the tumor antigen peptide or the derivative thereof, a CTL that recognizes a complex between the tumor antigen peptide or the derivative thereof and an HLA antigen, according to the present invention and the like can be also used as regents useful for investigations in the art.

BEST MODE FOR CARRYING OUT THE INVENTION

The present invention is further illustrated by the following examples, but is not limited by these examples in any respect.

EXAMPLE 1

Establishment of Cytotoxic T Lymphocytes (CTLs) Cell Line from Tumor-Infiltrating Lymphocytes (TILs) Derived from Lung Cancer A surgical sample taken from a patient with lung cancer was cut into small pieces, and then stirred in a culture fluid containing collagenase and DNAse to suspend cells. The cell suspension was centrifuged using Ficoll Conray solution to separate lymphocytes. The lymphocytes were cultured on 24-well plate in a culture medium consisting of 45% RPMI-1640, 45% AIM-V (GIBCO BRL), and 10% FCS supplemented with 100 U/ml interleukin-2 and 0.1 mM NEAA (GIBCO BRL) (hereinafter referred to as lymphocyte medium). During the first two days of the cultivation, an anti-CD3 antibody NU-T3 (Nichirei Corporation) was added to the culture medium at 1 μg/ml. The cultivation was continued for more than 30 days, and a CTL line that is reactive with some kinds of HLA-A24- or HLA-A2-positive cancer cell lines was established. The established CTL line was named KG-CTL and used in subsequent procedures. The reactivity of KG-CTL to each cancer cell line was examined by inoculating the cancer cell line into 96-well plate at $1 \times 10^4$, adding KG-CTL at $1 \times 10^5$/well thereto on the following day, culturing the same for additional 18 hours, and then determining amount of interferon-γ (IFN-γ) produced by KG-CTL in the recovered culture medium. Measurement of IFN-γ was conducted by enzyme immunoassay (ELISA). Specifically, an anti-human IFN-γ mouse monoclonal antibody was adsorbed on 96-well plate as solid-phased antibody, and after blocking non-specific bindings with bovine serum albumin, the antibody was allowed to bind to IFN-γ in the above-described sample. Anti-human IFN-γ rabbit polyclonal antibody as detection antibody was then allowed to bind, and after binding to an anti-rabbit immunoglobulin goat antibody labeled with alkaline phosphatase (Amersham), the chromophore was developed using Peroxidase Chromophoric Kit T (Sumitomo Bakelite), followed by measuring absorbance at 405 nm. The absorbance was compared with that obtained with standard IFN-γ to determine the amount of IFN-γ in the sample. Table 2 represents the reactivities of KG-CTL to various adenocarcinoma cell lines, whereas Table 3 represents the reactivities of KG-CTL to lymphoid cell lines

TABLE 2

| carcinoma cell clines | Amount of IFN-γ Produced by KG-CTL (pg/ml) | HLA-A type |
| --- | --- | --- |
| HT-1376 (bladder cancer cell line) | 4608 | 2402/2402 |
| 1–87 (lung cancer cell line) | 194 | 0207/1101 |
| 11–18 (lung cancer cell line) | 4632 | 0201/2402 |
| PC-9 (lung cancer cell line) | 1102 | 0206/2402 |
| LC-1 (lung cancer cell line) | 129 | 3101/3302 |
| YT-803 (lung cancer cell line) | 285 | 3101/3302 |
| 143B (osteosarcoma cell line) | 1547 | 0211/0211 |
| none (only KG-CTL) | 100 | — |

TABLE 3

| cell clines | Amount of IFN-γ Produced by KG-CTL (pg/ml) | HLA-A type |
| --- | --- | --- |
| SSB (B cell line[1]) | 5769 | 2402/2402 |
| Ban-B1 (B cell line[1]) | 78 | 3101/3302 |
| HPB-MLT (leukemia cell line) | 189 | 0101/0201 |
| MOLT-16 (leukemia cell line) | 13 | 2301/3002 |
| MT-2 (leukemia cell line) | 3495 | 2402/2402 |
| none (only KG-CTL) | 0 | — |

[1] B cell line derived from healthy subjects that is transformed with EB virus.

Table 2 shows that KG-CTL is strongly reactive to the HLA-A2402-positive cancer cells (HT-1376, 11–18, PC-9) to produce IFN-γ, and is also reactive to the HLA-A2-positive cancer cell (143B) to produce IFN-γ. Table 3 shows that KG-CTL is strongly reactive to the HLA-A2402-positive B cell line transformed with EB virus and leukemia cell (SSB, MT-2), and is also reactive to the HLA-A2-positive leukemia cell (HPB-MLT).

The established KG-CTL was deposited at The National Institute of Bioscience and Human Technology, Agency of Industrial Science and Technology (1-1-3 Higashi, Tsukuba, Ibaraki, Japan) (designation of microorganism: KG-CTL; deposition date: Jun. 19, 1998; deposit number: FERM P-16854; converted to international deposition on May 20, 1999 under deposit number: FERM BP-6725). Typing of HLA molecules for KG-CTL (conducted by Shionogi Co. Ltd. according to the description in Nakao et al., Cancer Res., 55:4248–4252 (1995)) revealed that its A locus is A0206 and A2402.

EXAMPLE 2

Identification of Tumor Antigen Proteins

According to the following procedures, a cDNA library was prepared from a bladder cancer cell line, HT-1376 (ATCC No. CRL1472), which was strongly reactive with KG-CTL as shown in Example 1.

First, Poly (A)+ mRNA was prepared from HT-1376 by isolation of total RNA fraction and purification on oligo (dT) column using mRNA Purification system (Pharmacia Biotech) according to the manufacturer's protocol. cDNAs having the Not I and Sca I adapters linked to each terminus were prepared from the mRNAs using SuperScript Plasmid System (GIBCO BRL) according to the manufacturer's protocol, and then ligated into the restriction sites Not I and Sal I of an expression vector, plasmid pSV-SPORT1 (GIBCO BRL), to yield recombinant plasmids. The recombinant plasmids were introduced into E. coli. ElectroMAX DH 10B™ cells (GIBCO BRL) using electric pulses in Gene Pulser (Bio-Rad), and the transformants into which the recombinant plasmids had been introduced were selected in LB medium (1% bacto-trypton, 0.5% yeast extract, 0.5% NaCl, pH7.3) containing ampicillin (50 µg/ml).

The recombinant plasmid DNAs were recovered as follows, from pools of about 100 transformants. A hundred transformants were introduced and cultured in each well of 96-well U-bottomed microplate containing LB medium plus ampicillin (50 µg/ml). Part of the culture was then transferred to another 96-well U-bottomed microplate containing 0.25 ml of TYGPN medium per well (F. M. Ausubel et al., *Current Protocols in Molecular Biology*, John Wiley & Sons, Inc.), and cultured at 37° C. for 48 hours. The remaining cultures in LB medium on the microplate were stored in frozen. Preparation of recombinant plasmid DNAs from the transformants cultured in TYGPN medium was achieved in the microplate by alkaline lysis method (F. M. Ausubel et al., *Current Protocols in Molecular Biology*, John Wiley & Sons, Inc.). The recombinant plasmid DNAs recovered by isopropanol precipitation were suspended in 50 µl of 10 mM Tris, 1 mM EDTA, pH 7.4, containing 20 ng/ml RNase.

On the other hand, according to the description of Nakao et al., *Cancer Res.*, 55: 4248–4252 (1995), a recombinant plasmid wherein cDNA for HLA-A2402 was incorporated into an expression vector pCR3 (INVITROGEN) was prepared from esophageal cancer cell line KE-4 deposited at The National Institute of Bioscience and Human Technology, Agency of Industrial Science and Technology (1-1-3 Higashi, Tsukuba, Ibaraki, Japan) (deposition date: May 23, 1997; deposit number: FERM BP-5955).

Subsequently, the recombinant plasmid for HT-1376 cDNA and the recombinant plasmid for HLA-A2402 cDNA were doubly transfected into cell line COS-7A (ATCC No. CRL1651) derived from Africa green monkey kidney using the Lipofectin method as follows. Eight thousands COS-7 cells were placed into each well of 96-well flat-bottomed microplate, and incubated for a day in 100 µl of RPMI 1640 medium containing 10% FCS. Using Lipofectamine reagent (GIBCO BRL), a 30 µl portion of the mixture (70 µl) consisting of 25 µl of the recombinant plasmid for HT-1376 cDNA corresponding to about 100 transformants, 10 µl (200 ng) of the recombinant plasmid for HLA-A2402 cDNA, and 35 µl of about 50-fold diluted Lipofectin reagent was added to COS-7 cells, and allowed to doubly transfect them.

Transfectants were prepared in duplicate. After five hours, the transfectants was added with 200 µl of culture medium containing 10% FCS, and further incubated at 37° C. for 48 hours. After removing the culture medium, $1.5 \times 10^5$ KG-CTL cells were added to each well, and cultured at 37° C. for 24 hours in 100 µl of culture medium containing 10% FCS and 25 U/ml IL-2. The culture medium was then recovered, and the amount of IFN-γ in the culture was measured by ELISA as described in Example 1.

About 100 transformants containing the recombinant plasmids for HT-1376 cDNA of the frozen-stored pools corresponding to the groups in which high production of IFN-γ was observed, were screened as follows. The pools of the transformants were plated on LB agar medium containing ampicillin (50 µg/ml) to obtain colonies. Four hundreds colonies for each group were cultured as described above so that a single kind of transformants is included in each well, thereby preparing recombinant plasmid DNAs for HT-1376 cDNA. According to a similar manner, COS-7 cells were doubly transfected with the recombinant plasmid for HT-1376 cDNA and the recombinant plasmid for HLA-A2402 cDNA, followed by co-cultivation with KG-CTL, and IFN-γ produced due to the KG-CTL reaction was quantitatively determined so as to select positive plasmids. In this manner, a single HT-1376 cDNA recombinant plasmid clone was selected and named 3D9. Further, similar procedures were once repeated with 3D9 to determine the amount of IFN-γ produced by KG-CTL. The results are shown in Table 4.

TABLE 4

| cells | Amount of IFN-γ produced by KG-CTL (pg/ml) |
|---|---|
| COS-7 + HLA-A2402 | 2152 |
| COS-7 + HLA-A2402 + 3D9 | 2379 |

When compared to COS-7 transfected with only HLA-A2402, KG-CTL reacted more strongly to COS-7 doubly transfected with HLA-A2402 and 3D9, and produced more IFN-γ. This result indicated that the protein encoded by 3D9 is a tumor antigen protein.

EXAMPLE 3

Determination of Base Sequence of Tumor Antigen Protein Gene

The base sequence of plasmid clone 3D9 that encodes the tumor antigen protein as obtained in Example 2 was determined using DyeDeoxy Terminator Cycle Sequencing kit (Perkin-Elmer). The base sequence thus determined (1711 base pairs) is shown in SEQ ID NO: 2, and the amino acid sequence (414 amino acids) encoded by the base sequence is shown in SEQ ID NO: 1. Comparison of the base sequence and the amino acid sequence to known sequences using WWW Entrez data base revealed that plasmid clone 3D9 is a novel gene. The novel tumor antigen protein encoded by 3D9 according to the present invention is named ART-1 (Adenocarcinoma antigen Recognized by T cells-1).

After the sequencing, E. coli JM109 (3D9), a transformant for storage that comprises a cDNA of novel tumor antigen protein ART-1 was prepared. E. coli JM109 (3D9) has been deposited at The National Institute of Bioscience and Human Technology (1-1-3 Higashi, Tsukuba, Ibaraki, Japan) (designation of microorganism: E. coli JM 109 (3D9), deposition date: Nov. 25, 1998; deposit number FERM BP-6929); this was converted to international deposition (date of conversion to international deposition: Nov. 4, 1999, deposit number: FERM BP-6929).

EXAMPLE 4

Selection of Candidate Peptides

There are certain rules (motifs) in the sequences of antigen peptides that should be bound and presented by HLA antigens. Regarding the motif for HLA-A24, it is known that in the sequence of peptides consisting of 8 to 11 amino acids, the amino acid at position 2 is tyrosine, phenylalanine, methionine, or tryptophan, and the amino acid at the C-terminus is phenylalanine, tryptophan, leucine, isoleucine, or methionine (*Immunogenetics,* 41:178, 1995; *J. Immunol.,* 152:3913, 1994; *J. Immunol.,* 155:4307, 1994).

According to the motifs, 16 peptide portions consisting of 8 to 11 peptides having the motifs for HLA-A24 binding were selected from the amino acid sequence of tumor antigen protein ART-1 of the present invention. Those 16 selected peptides are shown in SEQ ID NOs: 3–18. These peptides were synthesized by the Fmoc method as shown below.

Determination whether the peptides are a tumor antigen peptide was conducted as follows. $1 \times 10^4$ COS-7 cells were transfected with a recombinant plasmid for HLA-A2402 cDNA by the Lipofectin method to express the HLA-A2402 according to the literature (*J. Exp. Med.,* 187:277, 1998). To these cells, various peptides having a binding motif for HLA-A24 that had precedently synthesized were each added at 10 μM over two hours in order to pulse the cells. The cells were then cultured with $2 \times 10^4$ KG-CTLs for 18 hours, and the amount of IFN-γ produced by KG-CTL in the culture supernatant was determined by the ELISA method, thus identifying tumor antigen peptides.

Specific examples of synthesis of peptides having HLA-A24-binding motifs and of the determination of tumor antigen peptides are described in the following examples, which performed on three peptides, that is, a peptide comprising the sequence from position 170 to position 179 (SEQ ID NO: 3, hereinafter it may be referred to as "170–179"), a peptide comprising the sequence from position 188 to position 196 (SEQ ID NO: 4, hereinafter it may be referred to as "188–196"), and a peptide comprising the sequence from position 158 to position 165 (SEQ ID NO: 5, hereinafter it may be referred to as "158–165")in the amino acid sequence shown in SEQ ID NO: 1.

EXAMPLE 5

Synthesis of Gly-Phe-Asp-Cys-Ala-Asn-Glu-Ser-Val-Leu ("170–179". SEQ ID NO: 3)

Fmoc-Leu-Alko Resin (0.57 mmol/g, 100–200 mesh) was used as a resin. Using 50 mg of this resin, the synthesis was started according to Schedule 1 as described below (Table 5) to couple the following residues in order: Fmoc-Val-OH, Fmoc-Ser(tBu)-OH, Fmoc-Glu(OtBu)-OH, Fmoc-Asn-OH, Fmoc-Ala-OH, Fmoc-Cys(Trt)-OH, Fmoc-Asp(OtBu)-OH, Fmoc-Phe-OH, and Fmoc-Gly-OH. After the coupling, the procedures were conducted up to Step 3 of Schedule 1 to obtain a peptide resin.

To this peptide resin, 1 ml of Reagent K (the solution of 5% phenol, 5% thioanisole, 5% $H_2O$, and 2.5% ethanedithiol in TFA) was added and the mixture was allowed to react for 2.5 hours at room temperature. While cooling with ice, 10 ml of diethyl ether was added to the reaction, the mixture was stirred for 10 minutes, filtered, and washed with 10 ml of diethyl ether. To the filter cake, 10 ml of aqueous acetic acid was added, and the mixture was stirred for 30 minutes. The resin was then filtered, and washed with 4 ml of aqueous acetic acid. After lyophilizing the filtrate and the wash, the crude peptide obtained was dissolved in aqueous acetic acid, and injected into a reverse phase packing material, YMC-PACK ODS-A SH-363-5 column (30ϕ×250 mm) that had been pre-equilibrated with 0.1% aqueous TFA. The column was washed with 0.1% aqueous TFA, and elution at a flow rate of 7 ml/min was then conducted, while increasing the concentration of acetonitrile up to 40% over 240 minutes. The eluate was monitored by A 220 nm. The fractions containing the desired product were combined together and lyophilized to obtain 15.4 mg of Gly-Phe-Asp-Cys-Ala-Asn-Glu-Ser-Val-Leu (SEQ ID NO: 3)

The peptide obtained, Gly-Phe-Asp-Cys-Ala-Asn-Glu-Ser-Val-Leu (SEQ ID NO: 3), had a retention time of 19.9 minutes in an analysis using a reverse phase packing material, YMC-PACK ODS-AM AM-303 column (4.6ϕ×250 mm) eluted with a linear gradient of acetonitrile concentration from 0 to 60% containing 0.1% TFA, and the results of amino acid analysis (Cys being not detected) and mass spectrometry of the product were consistent with the theoretical values.

Amino Acid Analysis

Hydrolysis: 1% phenol/6N aqueous hydrochloric acid, 110° C., 24 hours;

Analysis method: the ninhydrin method;

*Reference amino acid; Theoretical values are indicated in parentheses:

Asx: 1.98 (2)

Ser: 0.78 (1)

Glx: 1.01 (1)

Gly: 0.99 (1)

Ala: 1.00 (1)

*Val: 1.00 (1)

Leu: 1.06 (1)

Phe: 1.01 (1)

Mass spectrum (FAB)

$[M+H]^+$: 1054

Table 5

| Schedule 1 | |
|---|---|
| Steps | Duration (min) × the number of treatments |
| 1. (washing) DMF 1.2 ml | 1 × 2 |
| 2. (deprotection) 50% piperidine/DMF | 12 × 1 |
| 3. (washing) DMF 1.2 ml | 1 × 7 |
| 4. (coupling) each amino-protected amino acid (5 equivalents)/NMP solution 0.9 ml, DIC (5 equivalents)/NMP solution 0.3 ml | 30 × 1 |
| 5. (washing) DMF 1.2 ml | 1 × 2 |
| 6. (coupling) each amino-protected amino acid (5 equivalents)/NMP solution 0.9 ml, DIC (5 equivalents)/NMP solution 0.3 ml | 30 × 1 |
| 7. (washing) DMF 1.2 ml | 1 × 4 |

EXAMPLE 6

Synthesis of Glu-Tyr-Cys-Leu-Lys-Phe-Thr-Lys-Leu ("188–196", SEQ ID NO. 4)

According to a similar manner to that described in Example 5, using 50 mg of Fmoc-Leu-Alko Resin (0.57 mmol/g, 100–200 mesh), Fmoc-Lys(Boc)-OH, Fmoc-Thr(tBu)-OH, Fmoc-Phe-OH, Fmoc-Lys(Boc)-OH, Fmoc-Leu-OH, Fmoc-Cys(Trt)-OH, Fmoc-Tyr(tBu)-OH, and Fmoc-Glu(OtBu)-OH were coupled in order, and the product was then deprotected. The crude peptide obtained was dissolved in aqueous acetic acid. The solution was separated into two portions, and each was purified with Sep-pak Vac (C18). Specifically, each portion was injected into the cartridge that had been pre-equilibrated with 0.1% aqueous TFA. The cartridge was washed three times with 10 ml of 0.1% aqueous TFA, and was eluted three times with 10 ml of 0.1% aqueous TFA-acetonitrile (1:1). The eluate was collected and lyophilized to obtain 37.5 mg of Glu-Tyr-Cys-Leu-Lys-Phe-Thr-Lys-Leu (SEQ ID NO: 4).

The peptide obtained, Glu-Tyr-Cys-Leu-Lys-Phe-Thr-Lys-Leu (SEQ ID NO: 4), had a retention time of 20.8 minutes in an analysis using a reverse phase packing material YMC-PACK ODS-AM-303 column (4.6φ×250 mm) eluted with a linear gradient of acetonitrile concentration from 0 to 60% containing 0.1% TFA, and the results of amino acid analysis (Cys being not detected) and mass spectrometry of the product were consistent with the theoretical values.

Amino Acid Analysis

Hydrolysis: 1% phenol/6N aqueous hydrochloric acid, 110° C., 24 hours;
Analysis method: the ninhydrin method;
*Reference amino acid; Theoretical values are indicated in parentheses:
Thr: 0.93 (1)
Glx: 0.96 (1)
*Leu: 2.00 (2)
Tyr: 0.83 (1)
Phe: 0.97 (1)
Lys: 1.88 (2)
Mass spectrum (FAB):
$[M+H]^+$: 1144

EXAMPLE 7

Synthesis of Leu-Tyr-Gln-Ala-Val-Ala-Thr-Ile ("158–165", SEQ ID NO: 5)

According to a similar manner to that described in Example 5, using 50 mg of Fmoc-Ile-Alko Resin (0.62 mmol/g, 100–200 mesh), Fmoc-Thr(tBu)-OH, Fmoc-Ala-OH, Fmoc-Val-OH, Fmoc-Ala-OH, Fmoc-Gln-OH, Fmoc-Tyr(tBu)-OH, and Fmoc-Leu-OH were coupled in order, and the product was then deprotected. The crude peptide obtained was dissolved in aqueous acetic acid and purified with Sep-pak Vac(C18) in accordance with a similar manner to that of Example 6, to obtain 12.4 mg of Leu-Tyr-Gln-Ala-Val-Ala-Thr-Ile (SEQ ID NO: 5).

The peptide obtained, Leu-Tyr-Gln-Ala-Val-Ala-Thr-Ile (SEQ ID NO: 5), had a retention time of 19.2 minutes in an analysis using a reverse phase packing material YMC-PACK ODS-AM column (4.6φ×250 mm) eluted with a linear gradient of acetonitrile concentration from 0 to 60% containing 0.1% TFA, and the results of amino acid analysis and mass spectrometry of the product were consistent with the theoretical values.

Amino Acid Analysis

Hydrolysis: 1% phenol/6N aqueous hydrochloric acid, 110° C., 24 hours;
Analysis method: the ninhydrin method;
Reference amino acid; Theoretical values are indicated in parentheses:
Thr: 0.91 (1)
Glx: 1.03 (1)
Ala: 2.07 (2)
*Val: 1.00 (1)
Ile: 0.99 (1)
Leu: 1.02 (1)
Tyr: 0.98 (1)
Mass spectrum (FAB):
$[M+H]^+$: 878

EXAMPLE 8

Identification of Tumor Antigen Peptides

The results of the determination regarding the three peptides as synthesized in Examples 5, 6 and 7 are shown in Table 6.

TABLE 6

| Pulsed Peptides | Amount of IFN-γ produced by KG-CTL in the response (pg/ml) |
| --- | --- |
| "158–165" | 289 |
| "170–179" | 458 |
| "188–196" | 399 |
| None | 117 |

KG-CTLs reacted more strongly to COS-7 cells pulsed with the peptides, "158–165", "170–179", and "188–196" in which a recombinant plasmid for the HLA-A2402 cDNA was transfected, compared to cells pulsed with no peptide. This result indicates that the three peptides "158–165", "170–179", and "188–196" function as an HLA-A24-restricted tumor antigen peptide.

EXAMPLE 9

CTL Induction from Peripheral Blood Lymphocytes by Tumor Antigen Peptides

The three peptides synthesized as shown in Examples 5–7 were investigated for their ability to induce antigen-specific CTLs from peripheral blood lymphocytes.

Using the Ficoll method, lymphocytes were separated from peripheral blood of healthy donors who were heterozygous for A24 in the HLA-A locus. The lymphocytes were placed into wells of a 24-well plate at $2\times10^6$ cells/well, and cultured in the lymphocyte medium. The above tumor antigen peptides were added to the culture medium at 10 μM to stimulate the peripheral blood lymphocytes. One week later, the above tumor antigen peptides were added to attain 10 μM together with about $2\times10^5$ cells of X-radiated (50 Gy) peripheral blood lymphocytes for the second stimulation. Additional one week later, the third stimulation was conducted in a similar manner. Cultured lymphocytes were harvested one week after the third stimulation. Using as target cells (1×10⁴ cells) MT-2, which is an HLA-A2402-positive leukemia cell line expressing the tumor antigen peptide, the amount of IFN-γ in the culture medium produced by the above lymphocytes (8×10⁴ cells) in response to the target cells was measured in accordance with ELISA method. The results are shown in Table 7.

TABLE 7

| Antigen Peptides | IFN-γ in Supernatant (pg/ml) |
|---|---|
| "158–165" | 330 |
| "170–179" | 237 |
| "188–196" | 147 |
| None | 3 |

Peripheral blood lymphocytes stimulated with the three peptides, "158–165", "170–179", and "188–196" produced IFN-γ in response to the target cell, but not peripheral blood lymphocytes with no stimulation, indicating that HLA-A24-restricted CTLs specific for tumor antigen peptide were induced.

Likewise, a similar experiment can be conducted using COS-7 cells (ATCC No. CRL1651) or VA-13 cells (RIKEN CELL BANK, The Institute of Physical and Chemical Research) into which an expression plasmid for HLA-A24 cDNA has been introduced and which have been pulsed with the above peptides, instead of MT-2 used in the present experiment (*J. Exp. Med.*, 187:277, 1998).

Sequence Listing Free Text

In the amino acid sequence shown in SEQ ID NO: 19, the second amino acid is phenylalanine, tyrosine, methionine or tryptophan, and the tenth amino acid is phenylalanine, leucine, isoleucine, tryptophan or methionine.

In the amino acid sequence shown in SEQ ID NO: 20, the second amino acid is phenylalanine, tyrosine, methionine or tryptophan, and the ninth amino acid is phenylalanine, leucine, isoleucine, tryptophan or methionine.

In the amino acid sequence shown in SEQ ID NO: 21, the second amino acid is phenylalanine, tyrosine, methionine or tryptophan, and the eighth amino acid is phenylalanine, leucine, isoleucine, tryptophan or methionine.

INDUSTRIAL APPLICABILITY

According to the present invention, a novel tumor antigen protein and gene therefor, tumor antigen peptides derived from said tumor antigen protein, and derivatives thereof, as well as medicaments, prophylactics, or diagnostics for tumors using such tumor antigen protein, gene, tumor antigen peptides, or derivatives thereof in vivo or in vitro, can be provided.

What is claimed is:

1. An isolated tumor antigen peptide consisting of 8 to 14 amino acids that is a fragment of the amino acid sequence of SEQ ID NO: 1 and that binds to an HLA antigen and is recognized by cytotoxic T lymphocytes.

2. The isolated tumor antigen peptide consisting of 8 to 14 amino acids of claim 1 wherein the HLA antigen is HLA-A24.

3. An isolated tumor antigen peptide consisting of 8 to 14 amino acids that is a fragment of the amino acid sequence of SEQ ID NO: 1, which fragment comprises a sequence selected from an amino acid sequence shown in any one of SEQ ID NOs: 3–18, or an isolated tumor antigen peptide consisting of 8 to 14 amino acids that is a fragment of the amino acid sequence of SEQ ID NO: 1, which comprises a sequence selected from an amino acid sequence shown in any one of SEQ ID NOs: 3–18 wherein the amino acid residue at position 2 is substituted by tyrosine, phenylalanine, methionine, or tryptophan, and/or the C-terminus is substituted by phenylalanine, leucine, isoleucine, tryptophan, or methionine, and which binds to an HLA antigen and is recognized by cytotoxic T lymphocytes.

4. The isolated tumor antigen peptide consisting of 8 to 14 amino acids of claim 3, which comprises a sequence selected from an amino acid sequence shown in any one of SEQ ID NOs: 3–5, or an isolated tumor antigen peptide consisting of 8 to 14 amino acids which comprises a sequence selected from an amino acid sequence shown in any one of SEQ ID NOs: 3–5 wherein the amino acid residue at position 2 is substituted by tyrosine, phenylalanine, methionine, or tryptophan, and/or the C-terminus is substituted by phenylalanine, leucine, isoleucine, tryptophan, or methionine, and which has the cytotoxic T lymphocyte binding properties of a peptide consisting of SEQ ID NO: 3, 4, or 5.

5. The isolated tumor antigen peptide consisting of 8 to 14 amino acids of claim 4, which comprises a sequence selected from an amino acid sequence shown in any one of SEQ ID NOs: 19–21.

6. A composition, which comprises as an active ingredient at least one substance selected from the isolated tumor antigen peptides consisting of 8 to 14 amino acids according to any one of claims 1 to 4 and 5.

7. A recombinant polypeptide obtainable by expressing a recombinant DNA comprising at least one of DNAs that encode the tumor antigen peptides consisting of 8 to 14 amino acids according to any one of claims 1 to 4 and 5.

8. A composition, which comprises as an active ingredient the recombinant polypeptide of claim 7.

9. A diagnostic agent for tumors, which comprises the tumor antigen peptide consisting of 8 to 14 amino acids according to any one of claims 1 to 4 and 5.

10. A diagnostic agent for tumors, which comprises the recombinant polypeptide of claim 7.

* * * * *

UNITED STATES PATENT AND TRADEMARK OFFICE
CERTIFICATE OF CORRECTION

PATENT NO. : 7,071,294 B1 Page 1 of 1
APPLICATION NO. : 09/857308
DATED : July 4, 2006
INVENTOR(S) : Kyogo Itoh et al.

It is certified that error appears in the above-identified patent and that said Letters Patent is hereby corrected as shown below:

On The Title Page, Item (87) should read:

(87)  PCT Pub. No. :  WO00/32770
      PCT Pub. Date :  June 8, 2000

Signed and Sealed this

Twenty-ninth Day of May, 2007

JON W. DUDAS
*Director of the United States Patent and Trademark Office*

SEQUENCE LISTING

<160> NUMBER OF SEQ ID NOS: 21

<210> SEQ ID NO 1
<211> LENGTH: 414
<212> TYPE: PRT
<213> ORGANISM: Homo sapiens

<400> SEQUENCE: 1

Met Asn Leu Gln Arg Tyr Trp Gly Glu Ile Pro Ile Ser Ser Ser Gln
                5                   10                  15

Thr Asn Arg Ser Ser Phe Asp Leu Leu Pro Arg Glu Phe Arg Leu Val
            20                  25                  30

Glu Val His Asp Pro Pro Leu His Gln Pro Ser Ala Asn Lys Pro Lys
        35                  40                  45

Pro Pro Thr Met Leu Asp Ile Pro Ser Glu Pro Cys Ser Leu Thr Ile
    50                  55                  60

His Thr Ile Gln Leu Ile Gln His Asn Arg Arg Leu Arg Asn Leu Ile
65                  70                  75                  80

Ala Thr Ala Gln Ala Gln Asn Gln Gln Gln Thr Glu Gly Val Lys Thr
                85                  90                  95

Glu Glu Ser Glu Pro Leu Pro Ser Cys Pro Gly Ser Pro Pro Leu Pro
            100                 105                 110

Asp Asp Leu Leu Pro Leu Asp Cys Lys Asn Pro Asn Ala Pro Phe Gln
        115                 120                 125

Ile Arg His Ser Asp Pro Glu Ser Asp Phe Tyr Arg Gly Lys Gly Glu
    130                 135                 140

Pro Val Thr Glu Leu Ser Trp His Ser Cys Arg Gln Leu Leu Tyr Gln
145                 150                 155                 160

Ala Val Ala Thr Ile Leu Ala His Ala Gly Phe Asp Cys Ala Asn Glu
                165                 170                 175

```
Ser Val Leu Glu Thr Leu Thr Asp Val Ala His Glu Tyr Cys Leu Lys
            180                 185                 190

Phe Thr Lys Leu Leu Arg Phe Ala Val Asp Arg Glu Ala Arg Leu Gly
            195                 200                 205

Gln Thr Pro Phe Pro Asp Val Met Glu Gln Val Phe His Glu Val Gly
            210                 215                 220

Ile Gly Ser Val Leu Ser Leu Gln Lys Phe Trp Gln His Arg Ile Lys
225                 230                 235                 240

Asp Tyr His Ser Tyr Met Leu Gln Ile Ser Lys Gln Leu Ser Glu Glu
            245                 250                 255

Tyr Glu Arg Ile Val Asn Pro Glu Lys Ala Thr Glu Asp Ala Lys Pro
            260                 265                 270

Val Lys Ile Lys Glu Pro Val Ser Asp Ile Thr Phe Pro Val Ser
            275                 280                 285

Glu Glu Leu Glu Ala Asp Leu Ala Ser Gly Asp Gln Ser Leu Pro Met
            290                 295                 300

Gly Val Leu Gly Ala Gln Ser Glu Arg Phe Pro Ser Asn Leu Glu Val
305                 310                 315                 320

Glu Ala Ser Pro Gln Ala Ser Ser Ala Glu Val Asn Ala Ser Pro Leu
            325                 330                 335

Trp Asn Leu Ala His Val Lys Met Glu Pro Gln Glu Ser Glu Glu Gly
            340                 345                 350

Asn Val Ser Gly His Gly Val Leu Gly Ser Asp Val Phe Glu Glu Pro
            355                 360                 365

Met Ser Gly Met Ser Glu Ala Gly Ile Pro Gln Ser Pro Asp Asp Ser
            370                 375                 380

Asp Ser Ser Tyr Gly Ser His Ser Thr Asp Ser Leu Met Gly Ser Ser
385                 390                 395                 400

Pro Val Phe Asn Gln Arg Cys Lys Lys Arg Met Arg Lys Ile
            405                 410

<210> SEQ ID NO 2
<211> LENGTH: 1711
<212> TYPE: DNA
<213> ORGANISM: Homo sapiens

<400> SEQUENCE: 2
acgcgatcct tgcctcaggc ctctcgaggt ccagacagcc gcccagcccg ctctgcgacg    60
cagcagtgaa tagtgtggta cctccttgtc tcggttcagg tccagacctc cccgtcttcc   120
ggctgccctg aacgtcaggc gacctcagga ccctgtgatt ggcgcctgcg ccggcggacc   180
gtgaccgagg aaaccctggg agggacttgg gcattccttg gctccgtgc ctgttcttcg    240 tgctcctttc gggcaaggat ctcacattat cagtctttga ccgacacaga atgcctggca   300
tttgataaat gtttgttgaa cttgaagaga catatggaca atg aat ctg caa aga   355
                                            Met Asn Leu Gln Arg
                                                              5 tac tgg gga gag ata cca ata tca tca agc cag acc aac aga agt tcc   403
Tyr Trp Gly Glu Ile Pro Ile Ser Ser Ser Gln Thr Asn Arg Ser Ser
             10                  15                  20 ttc gat ttg ctc cca cgg gag ttc cgt ctg gtg gaa gtc cat gac cca   451
Phe Asp Leu Leu Pro Arg Glu Phe Arg Leu Val Glu Val His Asp Pro
         25                  30                  35 ccc ctg cac caa ccc tca gcc aac aag ccg aag ccc ccc act atg ctg   499
Pro Leu His Gln Pro Ser Ala Asn Lys Pro Lys Pro Pro Thr Met Leu
     40                  45                  50
```

```
gac atc ccc tca gag cca tgt agt ctc acc atc cat acg att cag ttg      547
Asp Ile Pro Ser Glu Pro Cys Ser Leu Thr Ile His Thr Ile Gln Leu
     55                  60                  65 att cag cac aac cga cgt ctt cgc aac ctt att gcc aca gct cag gcc      595
Ile Gln His Asn Arg Arg Leu Arg Asn Leu Ile Ala Thr Ala Gln Ala
 70                  75                  80                  85 cag aat cag cag cag aca gaa ggt gta aaa act gaa gag agt gaa cct      643
Gln Asn Gln Gln Gln Thr Glu Gly Val Lys Thr Glu Glu Ser Glu Pro
                 90                  95                 100 ctt ccc tcg tgc cct ggg tca cct cct ctc cct gat gac ctc ctg cct      691
Leu Pro Ser Cys Pro Gly Ser Pro Pro Leu Pro Asp Asp Leu Leu Pro
            105                 110                 115 tta gat tgt aag aat ccc aat gca cca ttc cag atc cgg cac agt gac      739
Leu Asp Cys Lys Asn Pro Asn Ala Pro Phe Gln Ile Arg His Ser Asp
        120                 125                 130 cca gag agt gac ttt tat cgt ggg aaa ggg gaa cct gtg act gaa ctc      787
Pro Glu Ser Asp Phe Tyr Arg Gly Lys Gly Glu Pro Val Thr Glu Leu
    135                 140                 145 agc tgg cac tcc tgt cgg cag ctc ctc tac cag gca gtg gcc aca atc      835
Ser Trp His Ser Cys Arg Gln Leu Leu Tyr Gln Ala Val Ala Thr Ile
150                 155                 160                 165 ctg gcc cac gcg ggc ttt gac tgt gct aat gag agt gtc ctg gag acc      883
Leu Ala His Ala Gly Phe Asp Cys Ala Asn Glu Ser Val Leu Glu Thr
                170                 175                 180 cta act gat gtg gca cat gag tat tgc ctt aag ttt acc aag ttg ctg      931
Leu Thr Asp Val Ala His Glu Tyr Cys Leu Lys Phe Thr Lys Leu Leu
            185                 190                 195 cgt ttt gct gtg gac cgg gag gcc cgg ctg gga cag act cct ttt cct      979
Arg Phe Ala Val Asp Arg Glu Ala Arg Leu Gly Gln Thr Pro Phe Pro
        200                 205                 210 gat gtg atg gag cag gta ttc cat gaa gtg ggt att ggc agt gtg ctc     1027
Asp Val Met Glu Gln Val Phe His Glu Val Gly Ile Gly Ser Val Leu
    215                 220                 225 tcc ctc cag aag ttc tgg cag cac cgc atc aag gac tat cac agt tac     1075
Ser Leu Gln Lys Phe Trp Gln His Arg Ile Lys Asp Tyr His Ser Tyr
230                 235                 240                 245 atg cta cag att agt aag caa ctc tct gaa gaa tat gaa agg att gtc     1123
Met Leu Gln Ile Ser Lys Gln Leu Ser Glu Glu Tyr Glu Arg Ile Val
                250                 255                 260 aat cct gag aag gcc aca gag gac gct aaa cct gtg aag atc aag gag     1171
Asn Pro Glu Lys Ala Thr Glu Asp Ala Lys Pro Val Lys Ile Lys Glu
            265                 270                 275 gaa cct gtg agc gac atc act ttt cct gtc agt gag gag ctg gag gct     1219
Glu Pro Val Ser Asp Ile Thr Phe Pro Val Ser Glu Glu Leu Glu Ala
        280                 285                 290 gac ctt gct tct gga gac cag tca ctg cct atg gga gtg ctt ggg gct     1267
Asp Leu Ala Ser Gly Asp Gln Ser Leu Pro Met Gly Val Leu Gly Ala
    295                 300                 305 cag agc gaa cgc ttc cca tct aac ctg gag gtt gaa gct tca cca cag     1315
Gln Ser Glu Arg Phe Pro Ser Asn Leu Glu Val Glu Ala Ser Pro Gln
310                 315                 320                 325 gct tca agt gca gag gta aat gct tct cct ctt tgg aat ctg gcc cat     1363
Ala Ser Ser Ala Glu Val Asn Ala Ser Pro Leu Trp Asn Leu Ala His
                330                 335                 340 gtg aaa atg gag cct caa gaa agt gaa gaa ggc aat gtc tct ggg cat     1411
Val Lys Met Glu Pro Gln Glu Ser Glu Glu Gly Asn Val Ser Gly His
            345                 350                 355 ggt gtg ctg ggc agt gat gtc ttc gag gag cct atg tca ggc atg agt     1459
Gly Val Leu Gly Ser Asp Val Phe Glu Glu Pro Met Ser Gly Met Ser
```

-continued

```
                    360             365             370
gaa gct ggg att cct cag agc cct gat gac tca gat agc agc tat ggt   1507
Glu Ala Gly Ile Pro Gln Ser Pro Asp Asp Ser Asp Ser Ser Tyr Gly
    375                 380                 385 tcc cac tcc act gac agc ctc atg ggg tcc tcc cct gtt ttc aac cag   1555
Ser His Ser Thr Asp Ser Leu Met Gly Ser Ser Pro Val Phe Asn Gln
390                 395                 400                 405 cgc tgc aag aag agg atg agg aaa ata taaaaggaaa agagggagat         1602
Arg Cys Lys Lys Arg Met Arg Lys Ile
                410 gttttgtcca gacctactag acccaacaga aaaggttttt gtattagaat ctgtttcctt 1662 aaaaattgat tgactcctg ttcttaaaaa aaaaaaaaaa aaaaaaaaa              1711
```

<210> SEQ ID NO 3
<211> LENGTH: 10
<212> TYPE: PRT
<213> ORGANISM: Homo sapiens

<400> SEQUENCE: 3

Gly Phe Asp Cys Ala Asn Glu Ser Val Leu
                5                   10

<210> SEQ ID NO 4
<211> LENGTH: 9
<212> TYPE: PRT
<213> ORGANISM: Homo sapiens

<400> SEQUENCE: 4

Glu Tyr Cys Leu Lys Phe Thr Lys Leu
                5

<210> SEQ ID NO 5
<211> LENGTH: 8
<212> TYPE: PRT
<213> ORGANISM: Homo sapiens

<400> SEQUENCE: 5

Leu Tyr Gln Ala Val Ala Thr Ile
                5

<210> SEQ ID NO 6
<211> LENGTH: 9
<212> TYPE: PRT
<213> ORGANISM: Homo sapiens

<400> SEQUENCE: 6

Ser Phe Asp Leu Leu Pro Arg Glu Phe
                5

<210> SEQ ID NO 7
<211> LENGTH: 11
<212> TYPE: PRT
<213> ORGANISM: Homo sapiens

<400> SEQUENCE: 7

Ser Phe Asp Leu Leu Pro Arg Glu Phe Arg Leu
                5                   10

<210> SEQ ID NO 8
<211> LENGTH: 9
<212> TYPE: PRT
<213> ORGANISM: Homo sapiens

```
<400> SEQUENCE: 8

Leu Tyr Gln Ala Val Ala Thr Ile Leu
                5

<210> SEQ ID NO 9
<211> LENGTH: 10
<212> TYPE: PRT
<213> ORGANISM: Homo sapiens

<400> SEQUENCE: 9

Glu Tyr Cys Leu Lys Phe Thr Lys Leu Leu
                5                  10

<210> SEQ ID NO 10
<211> LENGTH: 10
<212> TYPE: PRT
<213> ORGANISM: Homo sapiens

<400> SEQUENCE: 10

Arg Phe Ala Val Asp Met Glu Gln Val Phe
                5                  10

<210> SEQ ID NO 11
<211> LENGTH: 10
<212> TYPE: PRT
<213> ORGANISM: Homo sapiens

<400> SEQUENCE: 11

Pro Phe Pro Asp Val Met Glu Gln Val Phe
                5                  10

<210> SEQ ID NO 12
<211> LENGTH: 11
<212> TYPE: PRT
<213> ORGANISM: Homo sapiens

<400> SEQUENCE: 12

Val Phe His Glu Val Gly Ile Gly Ser Val Leu
                5                  10

<210> SEQ ID NO 13
<211> LENGTH: 9
<212> TYPE: PRT
<213> ORGANISM: Homo sapiens

<400> SEQUENCE: 13

Asp Tyr His Ser Tyr Met Leu Gln Ile
                5

<210> SEQ ID NO 14
<211> LENGTH: 10
<212> TYPE: PRT
<213> ORGANISM: Homo sapiens

<400> SEQUENCE: 14

Ser Tyr Met Leu Gln Ile Ser Lys Gln Leu
                5                  10

<210> SEQ ID NO 15
<211> LENGTH: 10
<212> TYPE: PRT
<213> ORGANISM: Homo sapiens

<400> SEQUENCE: 15
```

Ser Tyr Gly Ser His Ser Thr Asp Ser Leu
                5                  10

<210> SEQ ID NO 16
<211> LENGTH: 8
<212> TYPE: PRT
<213> ORGANISM: Homo sapiens

<400> SEQUENCE: 16

Arg Tyr Trp Gly Glu Ile Pro Ile
                5

<210> SEQ ID NO 17
<211> LENGTH: 8
<212> TYPE: PRT
<213> ORGANISM: Homo sapiens

<400> SEQUENCE: 17

Lys Phe Thr Lys Leu Leu Arg Phe
                5

<210> SEQ ID NO 18
<211> LENGTH: 8
<212> TYPE: PRT
<213> ORGANISM: Homo sapiens

<400> SEQUENCE: 18

Thr Phe Pro Val Ser Glu Glu Leu
                5

<210> SEQ ID NO 19
<211> LENGTH: 10
<212> TYPE: PRT
<213> ORGANISM: Artificial Sequence
<220> FEATURE:
<221> NAME/KEY: VARIANT
<222> LOCATION: 2
<223> OTHER INFORMATION: Xaa is Phe, Tyr, Met or Trp.
<221> NAME/KEY: VARIANT
<222> LOCATION: 10
<223> OTHER INFORMATION: Xaa is Phe, Leu, Ile, Trp or Met.

<400> SEQUENCE: 19

Gly Xaa Asp Cys Ala Asn Glu Ser Val Xaa
                5                  10

<210> SEQ ID NO 20
<211> LENGTH: 9
<212> TYPE: PRT
<213> ORGANISM: Artificial Sequence
<220> FEATURE:
<221> NAME/KEY: VARIANT
<222> LOCATION: 2
<223> OTHER INFORMATION: Xaa is Phe, Tyr, Met or Trp.
<221> NAME/KEY: VARIANT
<222> LOCATION: 9
<223> OTHER INFORMATION: Xaa is Phe, Leu, Ile, Trp or Met.

<400> SEQUENCE: 20

Glu Xaa Cys Leu Lys Phe Thr Lys Xaa
                5

<210> SEQ ID NO 21
<211> LENGTH: 8
<212> TYPE: PRT
<213> ORGANISM: Artificial Sequence
<220> FEATURE:
<221> NAME/KEY: VARIANT

```
<222> LOCATION: 2
<223> OTHER INFORMATION: Xaa is Phe, Tyr, Met or Trp.
<221> NAME/KEY: VARIANT
<222> LOCATION: 8
<223> OTHER INFORMATION: Xaa is Phe, Leu, Ile, Trp or Met.

<400> SEQUENCE: 21

Leu Xaa Gln Ala Val Ala Thr Xaa
                 5
```